US011464430B2

(12) United States Patent
Budiman

(10) Patent No.: US 11,464,430 B2
(45) Date of Patent: Oct. 11, 2022

(54) METHOD AND DEVICE FOR PROVIDING OFFSET MODEL BASED CALIBRATION FOR ANALYTE SENSOR

(71) Applicant: Abbott Diabetes Care Inc., Alameda, CA (US)

(72) Inventor: Erwin Satrya Budiman, Fremont, CA (US)

(73) Assignee: Abbott Diabetes Care Inc., Alameda, CA (US)

(*) Notice: Subject to any disclaimer, the term of this patent is extended or adjusted under 35 U.S.C. 154(b) by 1029 days.

(21) Appl. No.: 16/147,087

(22) Filed: Sep. 28, 2018

(65) Prior Publication Data

US 2019/0035488 A1 Jan. 31, 2019

Related U.S. Application Data

(63) Continuation of application No. 14/017,195, filed on Sep. 3, 2013, now Pat. No. 10,089,446, which is a continuation of application No. 13/550,515, filed on Jul. 16, 2012, now Pat. No. 8,532,935, which is a continuation of application No. 12/362,479, filed on Jan. 29, 2009, now Pat. No. 8,224,415.

(51) Int. Cl.
*A61B 5/145* (2006.01)
*A61B 5/1486* (2006.01)
*A61B 5/1495* (2006.01)
*G16H 40/63* (2018.01)
*G16H 10/20* (2018.01)
*G16H 10/40* (2018.01)

(52) U.S. Cl.
CPC ........ *A61B 5/14532* (2013.01); *A61B 5/1495* (2013.01); *A61B 5/14865* (2013.01); *G16H 10/20* (2018.01); *G16H 10/40* (2018.01); *G16H 40/63* (2018.01); *A61B 2560/0223* (2013.01); *Y10T 436/144444* (2015.01)

(58) Field of Classification Search
None
See application file for complete search history.

(56) References Cited

U.S. PATENT DOCUMENTS

| | | |
|---|---|---|
| 3,581,062 A | 5/1971 | Aston |
| 3,926,760 A | 12/1975 | Allen et al. |
| 3,949,388 A | 4/1976 | Fuller |
| 3,960,497 A | 6/1976 | Acord et al. |
| 3,978,856 A | 9/1976 | Michel |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,441,968 A | 4/1984 | Emmer et al. |
| 4,462,048 A | 7/1984 | Ross |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,619,793 A | 10/1986 | Lee |
| 4,671,288 A | 6/1987 | Gough |
| 4,703,756 A | 11/1987 | Gough et al. |
| 4,711,245 A | 12/1987 | Higgins et al. |
| 4,731,051 A | 3/1988 | Fischell |
| 4,731,726 A | 3/1988 | Allen, III |
| 4,749,985 A | 6/1988 | Corsberg |
| 4,757,022 A | 7/1988 | Shults et al. |
| 4,759,366 A | 7/1988 | Callaghan |
| 4,777,953 A | 10/1988 | Ash et al. |
| 4,779,618 A | 10/1988 | Mund et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |

(Continued)

FOREIGN PATENT DOCUMENTS

| | | |
|---|---|---|
| EP | 0098592 | 1/1984 |
| EP | 0127958 | 12/1984 |

(Continued)

OTHER PUBLICATIONS

Wang et al. Glucose Biosensors: 40 Years of Advances and Challenges Electroanalysis vol. 13, pp. 983-988 (Year: 2001).*
Armour, J. C., et al., "Application of Chronic Intravascular Blood Glucose Sensor in Dogs", *Diabetes*, vol. 39, 1990, pp. 1519-1526.
Arnold, M. A., et al., "Selectivity Assessment of Noninvasive Glucose Measurements Based on Analysis of Multivariate Calibration Vectors", *Journal of Diabetes Science and Technology*, vol. 1, No. 4, 2007, pp. 454-462.
Bennion, N., et al., "Alternate Site Glucose Testing: A Crossover Design", *Diabetes Technology & Therapeutics*, vol. 4, No. 1, 2002, pp. 25-33.
Blank, T. B., et al., "Clinical Results From a Non-Invasive Blood Glucose Monitor", *Optical Diagnostics and Sensing of Biological Fluids and Glucose and Cholesterol Monitoring II*, Proceedings of SPIE, vol. 4624, 2002, pp. 1-10.

(Continued)

*Primary Examiner* — John S Brusca
(74) *Attorney, Agent, or Firm* — Baker Botts L.L.P.

(57) ABSTRACT

Methods and devices to detect analyte in body fluid are provided. Embodiments include processing sampled data from analyte sensor, determining a single, fixed, normal sensitivity value associated with the analyte sensor, estimating a windowed offset value associated with the analyte sensor for each available sampled data cluster, computing a time varying offset based on the estimated windowed offset value, and applying the time varying offset and the determined normal sensitivity value to the processed sampled data to estimate an analyte level for the sensor.

24 Claims, 6 Drawing Sheets

(56) References Cited

U.S. PATENT DOCUMENTS

| | | |
|---|---|---|
| 4,947,845 A | 8/1990 | Davis |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,113,869 A | 5/1992 | Nappholz et al. |
| 5,122,925 A | 6/1992 | Inpyn |
| 5,135,004 A | 8/1992 | Adams et al. |
| 5,148,812 A | 9/1992 | Verrier et al. |
| 5,165,407 A | 11/1992 | Wilson et al. |
| 5,199,428 A | 4/1993 | Obel et al. |
| 5,202,261 A | 4/1993 | Musho et al. |
| 5,203,326 A | 4/1993 | Collins |
| 5,204,264 A | 4/1993 | Kaminer et al. |
| 5,210,778 A | 5/1993 | Massart |
| 5,231,988 A | 8/1993 | Wernicke et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,313,953 A | 5/1994 | Yomtov et al. |
| 5,320,715 A | 6/1994 | Berg |
| 5,320,725 A | 6/1994 | Gregg et al. |
| 5,322,063 A | 6/1994 | Allen et al. |
| 5,328,460 A | 7/1994 | Lord et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,365,426 A | 11/1994 | Siegel et al. |
| 5,372,427 A | 12/1994 | Padovani et al. |
| 5,376,070 A | 12/1994 | Purvis et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,400,795 A | 3/1995 | Murphy et al. |
| 5,408,999 A | 4/1995 | Singh et al. |
| 5,411,647 A | 5/1995 | Johnson et al. |
| 5,425,749 A | 6/1995 | Adams |
| 5,425,868 A | 6/1995 | Pedersen |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,520,191 A | 5/1996 | Karlsson et al. |
| 5,531,878 A | 7/1996 | Vadgama et al. |
| 5,543,326 A | 8/1996 | Heller et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,890 A | 5/1997 | Carter et al. |
| 5,640,954 A | 6/1997 | Pfeiffer et al. |
| 5,653,239 A | 8/1997 | Pompei et al. |
| 5,660,163 A | 8/1997 | Schulman et al. |
| 5,665,222 A | 9/1997 | Heller et al. |
| 5,711,001 A | 1/1998 | Bussan et al. |
| 5,711,861 A | 1/1998 | Ward et al. |
| 5,720,295 A | 2/1998 | Greenhut et al. |
| 5,733,259 A | 3/1998 | Valcke et al. |
| 5,735,285 A | 4/1998 | Albert et al. |
| 5,741,211 A | 4/1998 | Renirie et al. |
| 5,772,586 A | 6/1998 | Heinonen et al. |
| 5,785,660 A | 7/1998 | van Lake et al. |
| 5,791,344 A | 8/1998 | Schulman et al. |
| 5,792,065 A | 8/1998 | Xue et al. |
| 5,820,551 A | 10/1998 | Hill et al. |
| 5,822,715 A | 10/1998 | Worthington et al. |
| 5,891,047 A | 4/1999 | Lander et al. |
| 5,899,855 A | 5/1999 | Brown |
| 5,914,026 A | 6/1999 | Blubaugh, Jr. et al. |
| 5,918,603 A | 7/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,957,854 A | 9/1999 | Besson et al. |
| 5,960,797 A | 10/1999 | Kramer et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,016,443 A | 1/2000 | Ekwall et al. |
| 6,021,350 A | 2/2000 | Mathson |
| 6,024,699 A | 2/2000 | Surwit et al. |
| 6,038,469 A | 3/2000 | Karlsson et al. |
| 6,049,727 A | 4/2000 | Crothall |
| 6,071,391 A | 6/2000 | Gotoh et al. |
| 6,073,031 A | 6/2000 | Helstab et al. |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,103,033 A | 8/2000 | Say et al. |
| 6,108,577 A | 8/2000 | Benser |
| 6,112,116 A | 8/2000 | Fischell |
| 6,115,622 A | 9/2000 | Minoz |
| 6,115,628 A | 9/2000 | Stadler et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,128,526 A | 10/2000 | Stadler et al. |
| 6,134,461 A | 10/2000 | Say et al. |
| 6,143,164 A | 11/2000 | Heller et al. |
| 6,144,837 A | 11/2000 | Quy |
| 6,159,147 A | 12/2000 | Lichter et al. |
| 6,161,095 A | 12/2000 | Brown |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,233,471 B1 | 5/2001 | Berner et al. |
| 6,233,486 B1 | 5/2001 | Ekwall et al. |
| 6,248,067 B1 | 6/2001 | Causey, III et al. |
| 6,249,705 B1 | 6/2001 | Snell |
| 6,254,586 B1 | 7/2001 | Mann et al. |
| 6,256,538 B1 | 7/2001 | Ekwall |
| 6,264,606 B1 | 7/2001 | Ekwall et al. |
| 6,270,455 B1 | 8/2001 | Brown |
| 6,272,379 B1 | 8/2001 | Fischell et al. |

(56) References Cited

U.S. PATENT DOCUMENTS

| | | |
|---|---|---|
| 6,275,717 B1 | 8/2001 | Gross et al. |
| 6,283,761 B1 | 9/2001 | Joao |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,361,503 B1 | 3/2002 | Starobin et al. |
| 6,366,794 B1 | 4/2002 | Moussy et al. |
| 6,377,828 B1 | 4/2002 | Chaiken et al. |
| 6,377,852 B1 | 4/2002 | Bornzin et al. |
| 6,377,894 B1 | 4/2002 | Deweese et al. |
| 6,379,301 B1 | 4/2002 | Worthington et al. |
| 6,381,493 B1 | 4/2002 | Stadler et al. |
| 6,387,048 B1 | 5/2002 | Schulman et al. |
| 6,405,066 B1 | 6/2002 | Essenpreis et al. |
| 6,413,393 B1 | 7/2002 | Van Antwerp et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,471,689 B1 | 10/2002 | Joseph et al. |
| 6,478,736 B1 | 11/2002 | Mault |
| 6,484,046 B1 | 11/2002 | Say et al. |
| 6,501,983 B1 | 12/2002 | Natarajan et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,540,891 B1 | 4/2003 | Stewart et al. |
| 6,544,212 B2 | 4/2003 | Galley et al. |
| 6,551,494 B1 | 4/2003 | Heller et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,622,045 B2 | 9/2003 | Snell et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,721,582 B2 | 4/2004 | Trepagnier et al. |
| 6,730,200 B1 | 5/2004 | Stewart et al. |
| 6,731,985 B2 | 5/2004 | Poore et al. |
| 6,733,446 B2 | 5/2004 | Lebel et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,912,413 B2 | 6/2005 | Rantala et al. |
| 6,923,763 B1 | 8/2005 | Kovatchev et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,954,662 B2 | 10/2005 | Freger et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,010,345 B2 | 3/2006 | Hill et al. |
| 7,011,630 B2 | 3/2006 | Desai et al. |
| 7,016,713 B2 | 3/2006 | Gardner et al. |
| 7,016,720 B2 | 3/2006 | Kroll |
| 7,022,072 B2 | 4/2006 | Fox et al. |
| 7,022,219 B2 | 4/2006 | Mansouri et al. |
| 7,024,245 B2 | 4/2006 | Lebel et al. |
| 7,025,425 B2 | 4/2006 | Kovatchev et al. |
| 7,029,443 B2 | 4/2006 | Kroll |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,052,472 B1 | 5/2006 | Miller et al. |
| 7,052,483 B2 | 5/2006 | Wojcik |
| 7,056,302 B2 | 6/2006 | Douglas |
| 7,074,307 B2 | 7/2006 | Simpson et al. |
| 7,076,300 B1 | 7/2006 | Kroll et al. |
| 7,081,195 B2 | 7/2006 | Simpson et al. |
| 7,092,891 B2 | 8/2006 | Maus et al. |
| 7,096,064 B2 | 8/2006 | Deno et al. |
| 7,098,803 B2 | 8/2006 | Mann et al. |
| 7,103,412 B1 | 9/2006 | Kroll |
| 7,108,778 B2 | 9/2006 | Simpson et al. |

(56) References Cited

U.S. PATENT DOCUMENTS

| | | |
|---|---|---|
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,134,999 B2 | 11/2006 | Brauker et al. |
| 7,136,689 B2 | 11/2006 | Shults et al. |
| 7,142,911 B2 | 11/2006 | Boileau et al. |
| 7,153,265 B2 | 12/2006 | Vachon |
| 7,167,818 B2 | 1/2007 | Brown |
| 7,171,274 B2 | 1/2007 | Starkweather et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,225,535 B2 | 6/2007 | Feldman et al. |
| 7,226,978 B2 | 6/2007 | Tapsak et al. |
| 7,258,673 B2 | 8/2007 | Racchini et al. |
| 7,267,665 B2 | 9/2007 | Steil et al. |
| 7,272,436 B2 | 9/2007 | Gill et al. |
| 7,276,029 B2 | 10/2007 | Goode, Jr. et al. |
| 7,278,983 B2 | 10/2007 | Ireland et al. |
| 7,295,867 B2 | 11/2007 | Berner et al. |
| 7,297,114 B2 | 11/2007 | Gill et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,402,153 B2 | 7/2008 | Steil et al. |
| 7,404,796 B2 | 7/2008 | Ginsberg |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,494,465 B2 | 2/2009 | Brister et al. |
| 7,497,827 B2 | 3/2009 | Brister et al. |
| 7,499,002 B2 | 3/2009 | Blasko et al. |
| 7,502,644 B2 | 3/2009 | Gill et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,524,287 B2 | 4/2009 | Bharmi |
| 7,547,281 B2 | 6/2009 | Hayes et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,620,438 B2 | 11/2009 | He |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,699,775 B2 | 4/2010 | Desai et al. |
| 7,699,964 B2 | 4/2010 | Feldman et al. |
| 7,711,493 B2 | 5/2010 | Bartkowiak et al. |
| 7,736,310 B2 | 6/2010 | Taub et al. |
| 7,751,864 B2 | 7/2010 | Buck, Jr. |
| 7,766,829 B2 | 8/2010 | Sloan et al. |
| 7,771,352 B2 | 8/2010 | Shults et al. |
| 7,774,145 B2 | 8/2010 | Bruaker et al. |
| 7,778,680 B2 | 8/2010 | Goode, Jr. et al. |
| 7,826,981 B2 | 11/2010 | Goode, Jr. et al. |
| 7,857,760 B2 | 12/2010 | Brister et al. |
| 7,866,026 B1 | 1/2011 | Wang et al. |
| 7,885,697 B2 | 2/2011 | Brister et al. |
| 7,889,069 B2 | 2/2011 | Fifolt et al. |
| 7,899,511 B2 | 3/2011 | Shults et al. |
| 7,905,833 B2 | 3/2011 | Brister et al. |
| 7,914,450 B2 | 3/2011 | Goode, Jr. et al. |
| 7,920,906 B2 | 4/2011 | Goode et al. |
| 7,938,797 B2 | 5/2011 | Estes |
| 7,946,984 B2 | 5/2011 | Brister et al. |
| 7,974,672 B2 | 7/2011 | Shults et al. |
| 8,060,173 B2 | 11/2011 | Goode, Jr. et al. |
| 8,116,837 B2 | 2/2012 | Huang |
| 8,140,312 B2 | 3/2012 | Hayter et al. |
| 8,160,900 B2 | 4/2012 | Taub et al. |
| 8,170,803 B2 | 5/2012 | Kamath et al. |
| 8,211,016 B2 | 7/2012 | Budiman |
| 8,216,137 B2 | 7/2012 | Budiman |
| 8,216,138 B1 | 7/2012 | McGarraugh et al. |
| 8,224,415 B2 | 7/2012 | Budiman et al. |
| 8,239,166 B2 | 8/2012 | Hayter et al. |
| 8,255,026 B1 | 8/2012 | Al-Ali |
| 8,282,549 B2 | 10/2012 | Brauker et al. |
| 8,376,945 B2 | 2/2013 | Hayter et al. |
| 8,444,560 B2 | 5/2013 | Hayter et al. |
| 8,457,703 B2 | 6/2013 | Al-Ali |
| 8,484,005 B2 | 7/2013 | Hayter et al. |
| 8,532,935 B2 | 9/2013 | Budiman |
| 8,543,354 B2 | 9/2013 | Luo et al. |
| 8,571,808 B2 | 10/2013 | Hayter |
| 8,612,163 B2 | 12/2013 | Hayter et al. |
| 8,657,746 B2 | 2/2014 | Roy |
| 8,682,615 B2 | 3/2014 | Hayter et al. |
| 9,060,719 B2 | 6/2015 | Hayter et al. |
| 9,113,828 B2 | 8/2015 | Budiman |
| 9,398,872 B2 | 7/2016 | Hayter et al. |
| 9,408,566 B2 | 8/2016 | Hayter et al. |
| 9,483,608 B2 | 11/2016 | Hayter et al. |
| 9,558,325 B2 | 1/2017 | Hayter et al. |
| 2001/0041831 A1 | 11/2001 | Starkweather et al. |
| 2002/0016534 A1 | 2/2002 | Trepagnier et al. |
| 2002/0019022 A1 | 2/2002 | Dunn et al. |
| 2002/0042090 A1 | 4/2002 | Heller et al. |
| 2002/0065454 A1 | 5/2002 | Lebel et al. |
| 2002/0068860 A1 | 6/2002 | Clark |
| 2002/0103499 A1 | 8/2002 | Perez et al. |
| 2002/0106709 A1 | 8/2002 | Potts et al. |
| 2002/0120186 A1 | 8/2002 | Keimel |
| 2002/0128594 A1 | 9/2002 | Das et al. |
| 2002/0143266 A1 | 10/2002 | Bock |
| 2002/0143372 A1 | 10/2002 | Snell et al. |
| 2002/0156355 A1 | 10/2002 | Gough |
| 2002/0161288 A1 | 10/2002 | Shin et al. |
| 2002/0169635 A1 | 11/2002 | Shillingburg |
| 2002/0193679 A1 | 12/2002 | Malave et al. |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0065308 A1 | 4/2003 | Lebel et al. |
| 2003/0100821 A1 | 5/2003 | Heller et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0235817 A1 | 12/2003 | Bartkowiak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |

(56) References Cited

U.S. PATENT DOCUMENTS

| | | |
|---|---|---|
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0077962 A1 | 4/2004 | Kroll |
| 2004/0078065 A1 | 4/2004 | Kroll |
| 2004/0093167 A1 | 5/2004 | Braig et al. |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0138716 A1 | 7/2004 | Kon et al. |
| 2004/0142403 A1 | 7/2004 | Hetzel et al. |
| 2004/0146909 A1 | 7/2004 | Duong et al. |
| 2004/0152622 A1 | 8/2004 | Keith et al. |
| 2004/0162678 A1 | 8/2004 | Hetzel et al. |
| 2004/0167801 A1 | 8/2004 | Say et al. |
| 2004/0171921 A1 | 9/2004 | Say et al. |
| 2004/0172307 A1 | 9/2004 | Gruber |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0204687 A1 | 10/2004 | Mogensen et al. |
| 2004/0208780 A1 | 10/2004 | Faries, Jr. et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0249420 A1 | 12/2004 | Olson et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0263354 A1 | 12/2004 | Mann et al. |
| 2004/0267300 A1 | 12/2004 | Mace |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0010269 A1 | 1/2005 | Lebel et al. |
| 2005/0016276 A1 | 1/2005 | Guan et al. |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0049473 A1 | 3/2005 | Desai et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0114068 A1 | 5/2005 | Chey et al. |
| 2005/0115832 A1 | 6/2005 | Simpson et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0196821 A1 | 9/2005 | Monfre et al. |
| 2005/0199494 A1 | 9/2005 | Say et al. |
| 2005/0203360 A1 | 9/2005 | Brauker et al. |
| 2005/0214892 A1 | 9/2005 | Kovatchev et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0277164 A1 | 12/2005 | Drucker et al. |
| 2005/0277912 A1 | 12/2005 | John |
| 2005/0287620 A1 | 12/2005 | Heller et al. |
| 2005/0288725 A1 | 12/2005 | Hettrick et al. |
| 2006/0001538 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025662 A1 | 2/2006 | Buse et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0091006 A1 | 5/2006 | Wang et al. |
| 2006/0142651 A1 | 6/2006 | Brister et al. |
| 2006/0155180 A1 | 7/2006 | Brister et al. |
| 2006/0166629 A1 | 7/2006 | Reggiardo |
| 2006/0167365 A1 | 7/2006 | Bharmi |
| 2006/0167517 A1 | 7/2006 | Gill et al. |
| 2006/0167518 A1 | 7/2006 | Gill et al. |
| 2006/0167519 A1 | 7/2006 | Gill et al. |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbies et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0193375 A1 | 8/2006 | Lee |
| 2006/0222566 A1 | 10/2006 | Brauker et al. |
| 2006/0224109 A1 | 10/2006 | Steil et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247685 A1 | 11/2006 | Bharmi |
| 2006/0247985 A1 | 11/2006 | Liamos et al. |
| 2006/0258929 A1 | 11/2006 | Goode et al. |
| 2006/0264785 A1 | 11/2006 | Dring et al. |
| 2006/0272652 A1 | 12/2006 | Stocker et al. |
| 2006/0281985 A1 | 12/2006 | Ward et al. |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0068807 A1 | 3/2007 | Feldman et al. |
| 2007/0071681 A1 | 3/2007 | Gadkar et al. |

(56) References Cited

U.S. PATENT DOCUMENTS

| | | |
|---|---|---|
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0095661 A1 | 5/2007 | Wang et al. |
| 2007/0106135 A1 | 5/2007 | Sloan et al. |
| 2007/0108048 A1 | 5/2007 | Wang et al. |
| 2007/0118030 A1 | 5/2007 | Bruce et al. |
| 2007/0118405 A1 | 5/2007 | Campbell et al. |
| 2007/0124002 A1 | 5/2007 | Estes et al. |
| 2007/0129621 A1 | 6/2007 | Kellogg et al. |
| 2007/0149875 A1 | 6/2007 | Ouyang et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179434 A1 | 8/2007 | Weinert et al. |
| 2007/0191701 A1 | 8/2007 | Feldman et al. |
| 2007/0199818 A1 | 8/2007 | Petyt et al. |
| 2007/0202562 A1 | 8/2007 | Curry et al. |
| 2007/0203407 A1 | 8/2007 | Hoss et al. |
| 2007/0203966 A1 | 8/2007 | Brauker et al. |
| 2007/0213657 A1 | 9/2007 | Jennewine et al. |
| 2007/0227911 A1 | 10/2007 | Wang et al. |
| 2007/0232877 A1 | 10/2007 | He |
| 2007/0232878 A1 | 10/2007 | Kovatchev et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0249922 A1 | 10/2007 | Peyser et al. |
| 2007/0255321 A1 | 11/2007 | Gerber et al. |
| 2007/0282299 A1 | 12/2007 | Hellwig |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0012701 A1 | 1/2008 | Kass et al. |
| 2008/0017522 A1 | 1/2008 | Heller et al. |
| 2008/0021666 A1 | 1/2008 | Goode, Jr. et al. |
| 2008/0021972 A1 | 1/2008 | Huelskamp et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0066305 A1 | 3/2008 | Wang et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0102441 A1 | 5/2008 | Chen et al. |
| 2008/0108942 A1 | 5/2008 | Brister et al. |
| 2008/0119703 A1 | 5/2008 | Brister et al. |
| 2008/0119708 A1 | 5/2008 | Budiman |
| 2008/0139910 A1 | 6/2008 | Mastrototaro et al. |
| 2008/0148873 A1 | 6/2008 | Wang |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208113 A1 | 8/2008 | Damiano et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234943 A1 | 9/2008 | Ray et al. |
| 2008/0242961 A1 | 10/2008 | Brister et al. |
| 2008/0242963 A1 | 10/2008 | Essenpreis et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0275313 A1 | 11/2008 | Brister et al. |
| 2008/0278332 A1 | 11/2008 | Fennel et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |

(56) References Cited

U.S. PATENT DOCUMENTS

| | | |
|---|---|---|
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054748 A1 | 2/2009 | Feldman et al. |
| 2009/0054749 A1 | 2/2009 | He |
| 2009/0054753 A1 | 2/2009 | Robinson et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0069649 A1 | 3/2009 | Budiman |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0099436 A1 | 4/2009 | Brister et al. |
| 2009/0105560 A1 | 4/2009 | Solomon |
| 2009/0105570 A1 | 4/2009 | Sloan et al. |
| 2009/0105636 A1 | 4/2009 | Hayter et al. |
| 2009/0112478 A1 | 4/2009 | Mueller, Jr. et al. |
| 2009/0112626 A1 | 4/2009 | Talbot et al. |
| 2009/0118589 A1 | 5/2009 | Ueshima et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0143725 A1 | 6/2009 | Peyser et al. |
| 2009/0149728 A1 | 6/2009 | Van Antwerp et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0182517 A1 | 7/2009 | Gandhi et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0253973 A1 | 10/2009 | Bashan et al. |
| 2009/0257911 A1 | 10/2009 | Thomas et al. |
| 2009/0281407 A1 | 11/2009 | Budiman |
| 2009/0287073 A1 | 11/2009 | Boock et al. |
| 2009/0287074 A1 | 11/2009 | Shults et al. |
| 2009/0294277 A1 | 12/2009 | Thomas et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063372 A1 | 3/2010 | Potts et al. |
| 2010/0064764 A1 | 3/2010 | Hayter et al. |
| 2010/0081906 A1 | 4/2010 | Hayter et al. |
| 2010/0081909 A1 | 4/2010 | Budiman et al. |
| 2010/0081953 A1 | 4/2010 | Syeda-Mahmood et al. |
| 2010/0121167 A1 | 5/2010 | McGarraugh et al. |
| 2010/0141656 A1 | 6/2010 | Krieftewirth |
| 2010/0152561 A1 | 6/2010 | Goodnow et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0191085 A1 | 7/2010 | Budiman |
| 2010/0204557 A1 | 8/2010 | Kiaie et al. |
| 2010/0230285 A1 | 9/2010 | Hoss et al. |
| 2010/0234710 A1 | 9/2010 | Budiman et al. |
| 2010/0261987 A1 | 10/2010 | Kamath et al. |
| 2010/0280441 A1 | 11/2010 | Willinska et al. |
| 2010/0312176 A1 | 12/2010 | Lauer et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0029247 A1 | 2/2011 | Kalathil |
| 2011/0040163 A1 | 2/2011 | Telson et al. |
| 2011/0060530 A1 | 3/2011 | Fennell |
| 2011/0077490 A1 | 3/2011 | Simpson et al. |
| 2011/0112696 A1 | 5/2011 | Yodfat et al. |
| 2011/0148905 A1 | 6/2011 | Simmons et al. |
| 2011/0208027 A1 | 8/2011 | Wagner et al. |
| 2011/0208155 A1 | 8/2011 | Palerm et al. |
| 2011/0257895 A1 | 10/2011 | Brauker et al. |
| 2011/0263958 A1 | 10/2011 | Brauker et al. |
| 2011/0320130 A1 | 12/2011 | Valdes et al. |
| 2012/0078071 A1 | 3/2012 | Bohm et al. |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0209029 A1 | 8/2012 | Ljuhs et al. |
| 2012/0215462 A1 | 8/2012 | Goode et al. |
| 2012/0245447 A1 | 9/2012 | Karan et al. |
| 2012/0277565 A1 | 11/2012 | Budiman |
| 2012/0283542 A1 | 11/2012 | McGarraugh |
| 2012/0318670 A1 | 12/2012 | Karinka et al. |
| 2013/0035575 A1 | 2/2013 | Mayou et al. |
| 2013/0137953 A1 | 5/2013 | Harper et al. |
| 2013/0231541 A1 | 9/2013 | Hayter et al. |
| 2013/0324823 A1 | 12/2013 | Koski et al. |
| 2014/0005499 A1 | 1/2014 | Catt et al. |
| 2014/0046160 A1 | 2/2014 | Terashima et al. |
| 2014/0088392 A1 | 3/2014 | Bernstein et al. |
| 2014/0121488 A1 | 5/2014 | Budiman |
| 2014/0221966 A1 | 8/2014 | Buckingham et al. |
| 2015/0216456 A1 | 8/2015 | Budiman |
| 2015/0241407 A1 | 8/2015 | Ou et al. |
| 2015/0366510 A1 | 12/2015 | Budiman |
| 2016/0022221 A1 | 1/2016 | Ou et al. |
| 2016/0302701 A1 | 10/2016 | Bhavaraju et al. |

FOREIGN PATENT DOCUMENTS

| | | |
|---|---|---|
| EP | 0320109 | 6/1989 |
| EP | 0353328 | 2/1990 |
| EP | 0390390 | 10/1990 |
| EP | 0396788 | 11/1990 |

(56) References Cited

FOREIGN PATENT DOCUMENTS

| | | |
|---|---|---|
| EP | 0472411 | 2/1992 |
| EP | 0286118 | 1/1995 |
| EP | 0867146 | 9/1998 |
| EP | 1048264 | 11/2000 |
| EP | 1419731 | 5/2004 |
| EP | 0939602 | 9/2004 |
| EP | 1850909 | 4/2010 |
| EP | 1677668 | 7/2010 |
| WO | WO-1996/025089 | 8/1996 |
| WO | WO-1996/035370 | 11/1996 |
| WO | WO-1997/015227 | 5/1997 |
| WO | WO-1998/035053 | 8/1998 |
| WO | WO-1999/056613 | 11/1999 |
| WO | WO-2000/049940 | 8/2000 |
| WO | WO-2000/059370 | 10/2000 |
| WO | WO-2000/074753 | 12/2000 |
| WO | WO-2001/052935 | 7/2001 |
| WO | WO-2001/054753 | 8/2001 |
| WO | WO-2002/016905 | 2/2002 |
| WO | WO-2002/058537 | 8/2002 |
| WO | WO-2003/076893 | 9/2003 |
| WO | WO-2003/082091 | 10/2003 |
| WO | WO-2004/060455 | 7/2004 |
| WO | WO-2005/010756 | 2/2005 |
| WO | WO-2005/065542 | 7/2005 |
| WO | WO-2006/024671 | 3/2006 |
| WO | WO-2006/081336 | 8/2006 |
| WO | WO-2006/086423 | 8/2006 |
| WO | WO-2006/124099 | 11/2006 |
| WO | WO-2007/097754 | 8/2007 |
| WO | WO-2008/086541 | 7/2008 |

OTHER PUBLICATIONS

Boyne, M. S., et al., "Timing of Changes in Interstitial and Venous Blood Glucose Measured With a Continuous Subcutaneous Glucose Sensor", *Diabetes*, vol. 52, Nov. 2003, pp. 2790-2794.

Bremer, T. M., et al., "Benchmark Data from the Literature for Evaluation of New Glucose Sensing Technologies", *Diabetes Technology & Therapeutics*, vol. 3, No. 3, 2001, pp. 409-418.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

Choleau, C., et al., "Calibration of a Subcutaneous Amperometric Glucose Sensor Implanted for 7 Days in Diabetic Patients Part 2. Superiority of the One-Point Calibration Method", *Biosensors and Bioelectronics*, vol. 17, No. 8, 2002, pp. 647-654.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Eren-Oruklu, M., et al., "Estimation of Future Glucose Concentrations with Subject-Specific Recursive Linear Models", *Diabetes Technology & Therapeutics* vol. 11(4), 2009, pp. 243-253.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Georgescu, B., et al., "Real-Time Multimodel Tracking of Myocardium in Echocardiography Using Robust Information Fusion", *Medical Image Computing and Computer-Assisted Intervention*, 2004, pp. 777-785.

Goldman, J. M., et al., "Masimo Signal Extraction Pulse Oximetry", *Journal of Clinical Monitoring and Computing*, vol. 16, No. 7, 2000, pp. 475-483.

Guerci, B., et al., "Clinical Performance of CGMS in Type 1 Diabetic Patients Treated by Continuous Subcutaneous Insulin Infusion Using Insulin Analogs", *Diabetes Care*, vol. 26, 2003, pp. 582-589.

Hovorka, R., et al., "Nonlinear Model Predictive Control of Glucose Concentration in Subjects with Type 1 Diabetes", *Physiological Measurement*, vol. 55, Jul. 2004, pp. 905-920.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Kovatchev, B. P., et al., "Evaluating the Accuracy of Continuous Glucose-Monitoring Sensors", *Diabetes Care*, vol. 27, No. 8, 2004, pp. 1922-1928.

Kovatchev, B. P., et al., "Graphical and Numerical Evaluation of Continuous Glucose Sensing Time Lag", *Diabetes Technology & Therapeutics*, vol. 11, No. 3, Feb. 2009, pp. 139-143.

Kuure-Kinsey, M., et al., "A Dual-Rate Kalman Filter for Continuous Glucose Monitoring", *Proceedings of the 28th IEEE, EMBS Annual International Conference*, New York City, 2006, pp. 63-66.

Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Maher, "A Method for Extrapolation of Missing Digital Audio Data", *Preprints of Papers Presented at the AES Convention*, 1993, pp. 1-19.

Maher, "Audio Enhancement using Nonlinear Time-Frequency Filtering", *AES 26th International Conference*, 2005, pp. 1-9.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

Mcgarraugh, G., et al., "Glucose Measurements Using Blood Extracted from the Forearm and the Finger", *TheraSense Inc.*, 2001, 16 Pages.

Mcgarraugh, G., et al., "Physiological Influences on Off-Finger Glucose Testing", *Diabetes Technology & Therapeutics*, vol. 3, No. 3, 2001, pp. 367-376.

Mckean, B. D., et al., "A Telemetry—Instrumentation System for Chronically Implanted Glucose and Oxygen Sensors", *IEEE Transactions on Biomedical Engineering*, vol. 35, No. 7, 1988, pp. 526-532.

Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.

Mougiakakou, et al., "A Real Time Simulation Model of Glucose-Insulin Metabolism for Type 1 Diabetes Patients", *Proceedings of the 2005 IEEE*, 2005, pp. 298-301.

Panteleon, A. E., et al., "The Role of the Independent Variable to Glucose Sensor Calibration", *Diabetes Technology & Therapeutics*, vol. 5, No. 3, 2003, pp. 401-410.

Parker, R., et al., "Robust H∞ Glucose Control in Diabetes Using a Physiological Model", *AIChE Journal*, vol. 46, No. 12, 2000, pp. 2537-2549.

(56) References Cited

OTHER PUBLICATIONS

Pickup, J., et al., "Implantable Glucose Sensors: Choosing the Appropriate Sensing Strategy", *Biosensors*, vol. 3, 1987/88, pp. 335-346.
Pickup, J., et al., "In Vivo Molecular Sensing in Diabetes Mellitus: An Implantable Glucose Sensor with Direct Electron Transfer", *Diabetologia*, vol. 32, 1989, pp. 213-217.
Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Roe, J. N., et al., "Bloodless Glucose Measurements", *Critical Review in Therapeutic Drug Carrier Systems*, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.
Shaw, G. W., et al., "In Vitro Testing of a Simply Constmcted, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.
Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Steil, G. M., et al., "Closed-Loop Insulin Delivery—the Path of Physiological Glucose Control", *Advanced Drug Delivery Reviews*, vol. 56, 2004, pp. 125-144.
Steil, G. M., et al., "Determination of Plasma Glucose During Rapid Glucose Excursions with a Subcutaneous Glucose Sensor", *Diabetes Technology & Therapeutics*, vol. 5, No. 1, 2003, pp. 27-31.
Sternberg, R., et al., "Study and Development of Multilayer Needle-Type Enzyme-Based Glucose Microsensors", *Biosensors*, vol. 4, 1988, pp. 27-40.
Thompson, M., et al., "In Vivo Probes: Problems and Perspectives", *Clinical Biochemistry*, vol. 19, 1986, pp. 255-261.
Turner, A., et al., "Diabetes Mellitus: Biosensors for Research and Management", *Biosensors*, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.
Velho, G., et al., "Strategies for Calibrating a Subcutaneous Glucose Sensor", *Biomedica Biochimica Acta*, vol. 48, 1989, pp. 957-964.
Whipple, G., "Low Residual Noise Speech Enhancement Utilizing Time-Frequency", *Proceedings of the International Conference on Acoustics, Speech, and Signal Processing*, vol. 19, 1994, pp. 15-18.
Wilson, G. S., et al., "Progress Toward the Development of an Implantable Sensor for Glucose", *Clinical Chemistry*, vol. 38, No. 9, 1992, pp. 1613-1617.
Wolfe, P. J., et al., "Interpolation of Missing Data Values for Audio Signal Restoration Using a Gabor Regression Model", *2005 IEEE International Conference on Acoustics, Speech, and Signal Processing*, vol. 5, 2005, pp. 517-520.
PCT Application No. PCT/US2010/022669, International Preliminary Report on Patentability and Written Opinion of The International Searching Authority dated Aug. 11, 2011.
PCT Application No. PCT/US2010/022669, International Search Report and Written Opinion of The International Searching Authority dated Mar. 23, 2010.
U.S. Appl. No. 12/362,479, Notice of Allowance dated May 25, 2012.
U.S. Appl. No. 12/362,479, Office Action dated Oct. 7, 2011.
U.S. Appl. No. 13/550,515, Notice of Allowance dated Jun. 24, 2013.
U.S. Appl. No. 13/550,515, Office Action dated Dec. 19, 2012.
U.S. Appl. No. 14/017,195, Advisory Action dated Feb. 22, 2017.
U.S. Appl. No. 14/017,195, Notice of Allowance dated Jun. 27, 2018.
U.S. Appl. No. 14/017,195, Office Action dated Dec. 15, 2016.
U.S. Appl. No. 14/017,195, Office Action dated Jul. 22, 2016.
U.S. Appl. No. 14/017,195, Office Action dated Sep. 26, 2017.
U.S. Appl. No. 14/077,004, Office Action dated Jul. 26, 2016.

\* cited by examiner

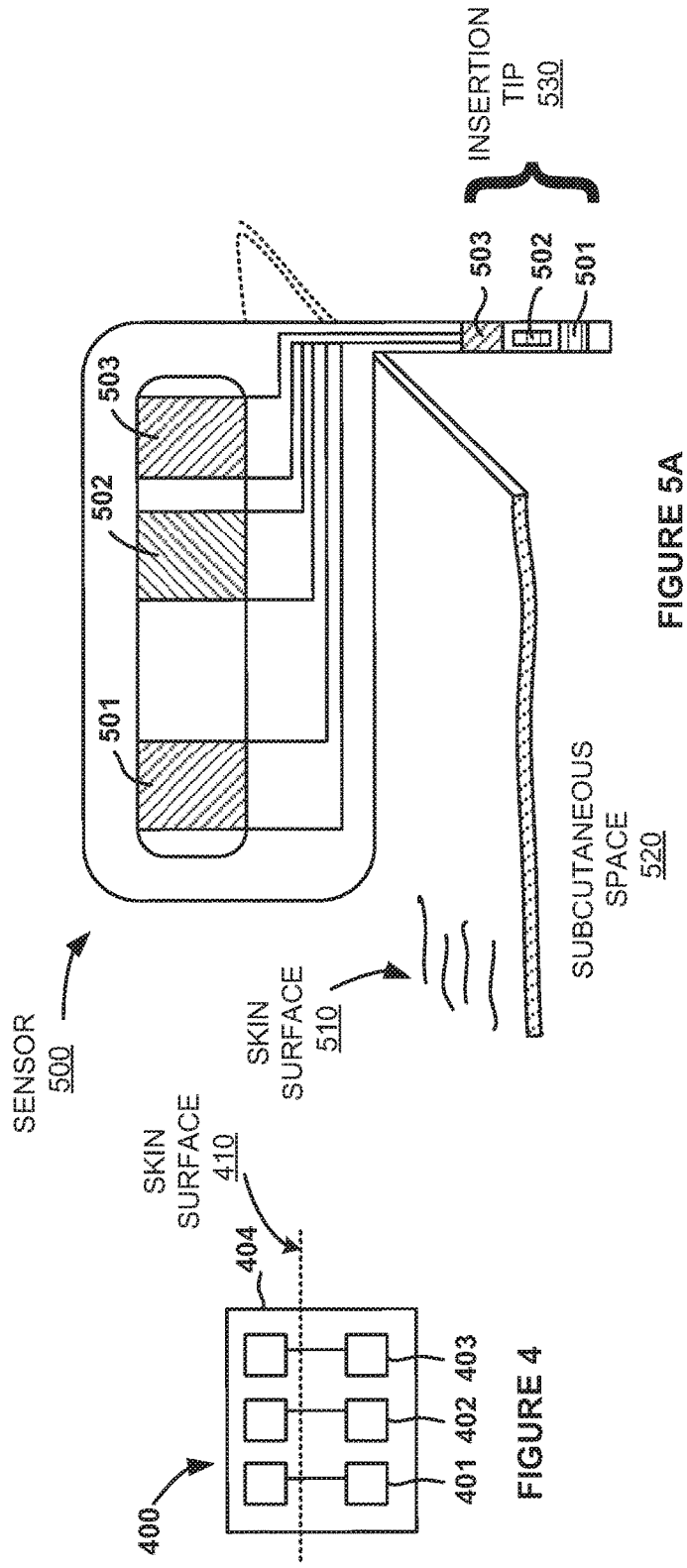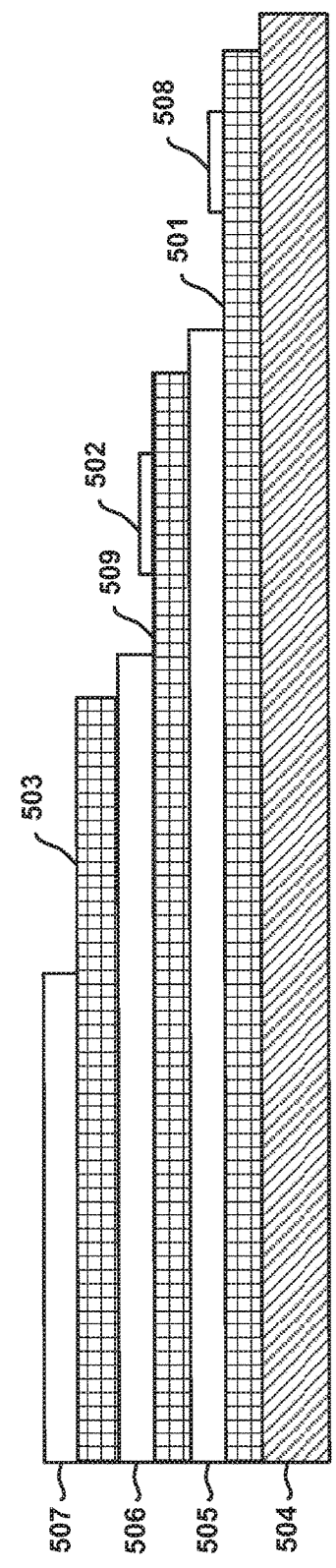

US 11,464,430 B2

METHOD AND DEVICE FOR PROVIDING OFFSET MODEL BASED CALIBRATION FOR ANALYTE SENSOR

RELATED APPLICATIONS

The present application is a continuation of U.S. patent application Ser. No. 14/017,195 filed Sep. 3, 2013, now U.S. Pat. No. 10,089,446, which is a continuation of U.S. patent application Ser. No. 13/550,515 filed Jul. 16, 2012, now U.S. Pat. No. 8,532,935, which is a continuation of U.S. patent application Ser. No. 12/362,479 filed Jan. 29, 2009, now U.S. Pat. No. 8,224,415, entitled "Method and Device for Providing Offset Model Based Calibration for Analyte Sensor", the disclosures of each of which are incorporated herein by reference for all purposes.

BACKGROUND

The detection of the level of glucose or other analytes, such as lactate, oxygen or the like, in certain individuals is vitally important to their health. For example, the monitoring of glucose is particularly important to individuals with diabetes. Diabetics may need to monitor glucose levels to determine when insulin is needed to reduce glucose levels in their bodies or when additional glucose is needed to raise the level of glucose in their bodies.

Devices have been developed for continuous or automatic monitoring of analytes, such as glucose, in bodily fluid such as in the blood stream or in interstitial fluid. Some of these analyte measuring devices are configured so that at least a portion of the devices are positioned below a skin surface of a user, e.g., in a blood vessel or in the subcutaneous tissue of a user.

Following the sensor insertion, the resulting potential trauma to the skin and/or underlying tissue, for example, by the sensor introducer and/or the sensor itself, may, at times, result in instability of signals monitored by the sensor. This may occur in a number of analyte sensors, but not in all cases. This instability is characterized by a decrease in the sensor signal, and when this occurs, generally, the analyte levels monitored may not be reported, recorded or output to the user.

SUMMARY

Embodiments of the subject disclosure include device and methods of determining early signal attenuation (ESA) in signals from analyte sensors. More specifically, embodiments include method, device and system for processing sampled data from analyte sensor, determining a single, fixed, normal sensitivity value associated with the analyte sensor, estimating a windowed offset value associated with the analyte sensor for each available sampled data cluster, computing a time varying offset based on the estimated windowed offset value, and applying the time varying offset and the determined normal sensitivity value to the processed sampled data to estimate an analyte level for the sensor.

Also provided are systems, computer program products, and kits.

BRIEF DESCRIPTION OF THE DRAWINGS

FIG. 4 shows a schematic diagram of an embodiment of an analyte sensor according to the present disclosure;

FIGS. 5A-5B show a perspective view and a cross sectional view, respectively of an embodiment the analyte sensor of FIG. 4;

DETAILED DESCRIPTION

Figure 1:
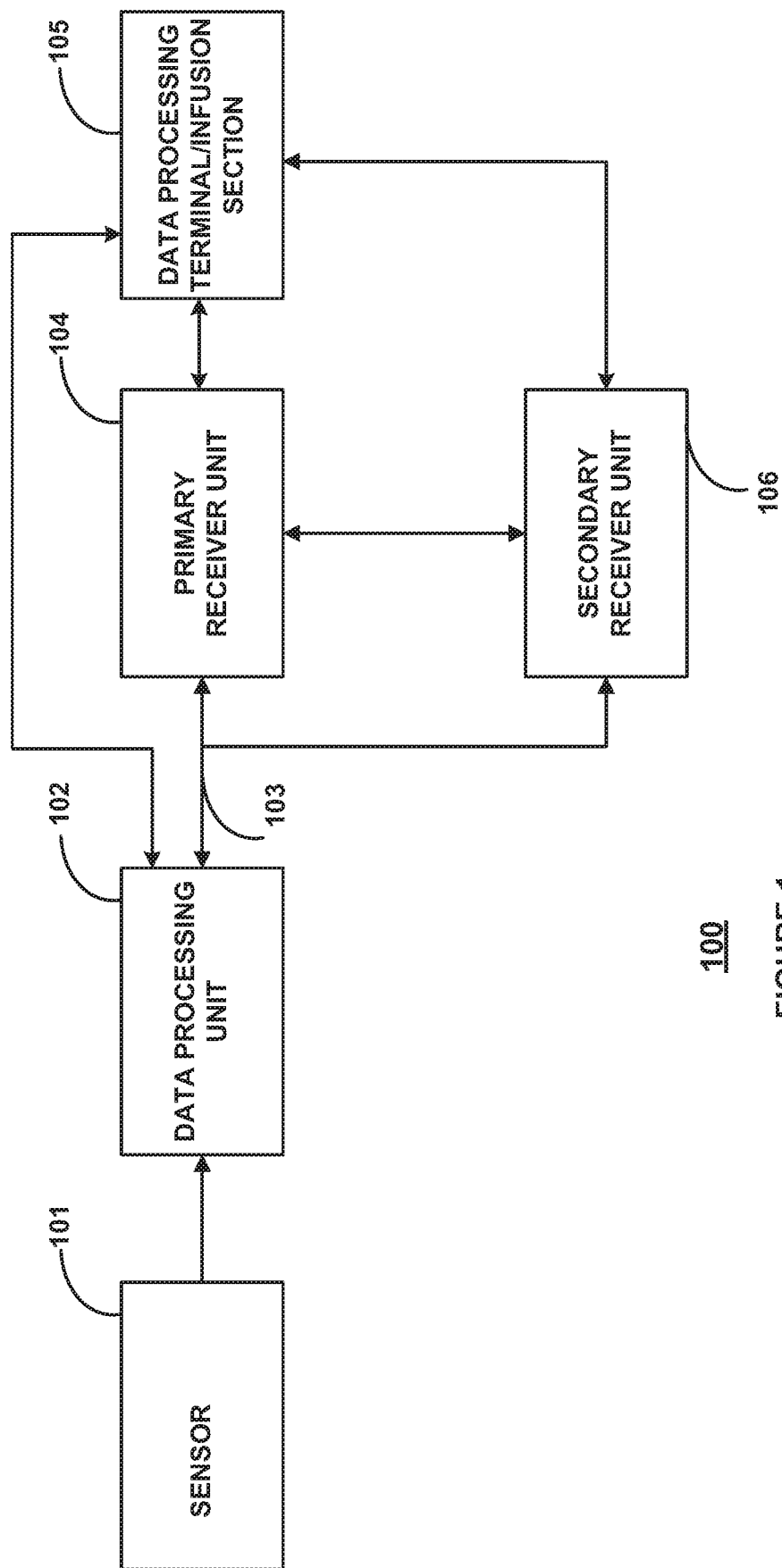
FIG. 1 shows a block diagram of an embodiment of a data monitoring and management system according to the present disclosure.

Before the present disclosure is described in additional detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. That the upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Generally, embodiments of the present disclosure relate to methods and devices for detecting at least one analyte such as glucose in body fluid. In certain embodiments, the present disclosure relates to the continuous and/or automatic in vivo monitoring of the level of an analyte using an analyte sensor.

Accordingly, embodiments include analyte monitoring devices and systems that include an analyte sensor—at least a portion of which is positionable beneath the skin of the user—for the in vivo detection, of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a transmitter, receiver, transceiver, processor, etc. The sensor may be, for example, subcutaneously positionable in a patient for the continuous or periodic monitoring of a level of an analyte in a patient's interstitial fluid. For the purposes of this description, continuous monitoring and periodic monitoring will be used interchangeably, unless noted otherwise. The analyte level may be correlated and/or converted to analyte levels in blood or other fluids. In certain embodiments, an analyte sensor may be positioned in contact with interstitial fluid to detect the level of glucose, which detected glucose may be used to infer the glucose level in the patient's bloodstream. Analyte sensors may be insertable into a vein, artery, or other portion of the body containing fluid. Embodiments of the analyte sensors of the subject disclosure may be configured for monitoring the level of the analyte over a time period which may range from minutes, hours, days, weeks, or longer.

Of interest are analyte sensors, such as glucose sensors, that are capable of in vivo detection of an analyte for about one hour or more, e.g., about a few hours or more, e.g., about a few days or more, e.g., about three or more days, e.g., about five days or more, e.g., about seven days or more, e.g., about several weeks or at least one month. Future analyte levels may be predicted based on information obtained, e.g., the current analyte level at time $t_0$, the rate of change of the analyte, etc. Predictive alarms may notify the user of predicted analyte levels that may be of concern prior in advance of the analyte level reaching the future level. This enables the user an opportunity to take corrective action.

FIG. 1 shows a data monitoring and management system such as, for example, an analyte (e.g., glucose) monitoring system 100 in accordance with certain embodiments. Embodiments of the subject disclosure are further described primarily with respect to glucose monitoring devices and systems, and methods of glucose detection, for convenience only and such description is in no way intended to limit the scope of the disclosure. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

The analyte monitoring system 100 includes a sensor 101, a data processing unit 102 connectable to the sensor 101, and a primary receiver unit 104 which is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bi-directional communication. Further, the data processing unit 102 may include a transmitter or a transceiver to transmit and/or receive data to and/or from the primary receiver unit 104, the data processing terminal 105 or optionally the secondary receiver unit 106.

Also shown in FIG. 1 is an optional secondary receiver unit 106 which is operatively coupled to the communication link and configured to receive data transmitted from the data processing unit 102. The secondary receiver unit 106 may be configured to communicate with the primary receiver unit 104, as well as the data processing terminal 105. The secondary receiver unit 106 may be configured for bi-directional wireless communication with each of the primary receiver unit 104 and the data processing terminal 105. As discussed in further detail below, in certain embodiments the secondary receiver unit 106 may be a de-featured receiver as compared to the primary receiver, i.e., the secondary receiver may include a limited or minimal number of functions and features as compared with the primary receiver unit 104. As such, the secondary receiver unit 106 may include a smaller (in one or more, including all, dimensions), compact housing or embodied in a device such as a wrist watch, arm band, etc., for example. Alternatively, the secondary receiver unit 106 may be configured with the same or substantially similar functions and features as the primary receiver unit 104. The secondary receiver unit 106 may include a docking portion to be mated with a docking cradle unit for placement by, e.g., the bedside for night time monitoring, and/or bi-directional communication.

Only one sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105. Multiple sensors may be positioned in a patient for analyte monitoring at the same or different times. In certain embodiments, analyte information obtained by a first positioned sensor may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The sensor 101 may be configured to at least periodically sample the analyte level of the user and convert the sampled analyte level into a corresponding signal for transmission by the data processing unit 102. The data processing unit 102 is coupleable to the sensor 101 so that both devices are positioned in or on the user's body, with at least a portion of the analyte sensor 101 positioned transcutaneously. The data processing unit 102 performs data processing functions, where such functions may include but are not limited to, filtering and encoding of data signals, each of which corresponds to a sampled analyte level of the user, for transmission to the primary receiver unit 104 via the communication link 103. In one embodiment, the sensor 101 or the data processing unit 102 or a combined sensor/data processing unit may be wholly implantable under the skin layer of the user.

In one aspect, the primary receiver unit 104 may include an analog interface section including a radio frequency (RF) receiver and an antenna that is configured to communicate with the data processing unit 102 via the communication link 103, a data processing section for processing the received data from the data processing unit 102 such as data decoding, error detection and correction, data clock generation, and/or data bit recovery.

In operation, the primary receiver unit 104 in certain embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor 101.

Referring again to FIG. 1, the data processing terminal 105 may include a personal computer, a portable computer such as a laptop or a handheld device (e.g., personal digital assistants (PDAs), telephone such as a cellular phone (e.g., a multimedia and Internet-enabled mobile phone such as an iPhone or similar phone), mp3 player, pager, and the like), drug delivery device, each of which may be configured for data communication with the receiver via a wired or a wireless connection. Additionally, the data processing terminal 105 may further be connected to a data network (not shown) for storing, retrieving, updating, and/or analyzing data corresponding to the detected analyte level of the user.

The data processing terminal 105 may include an infusion device such as an insulin infusion pump or the like, which may be configured to administer insulin to patients, and which may be configured to communicate with the primary receiver unit 104 for receiving, among others, the measured analyte level. Alternatively, the primary receiver unit 104 may be configured to integrate an infusion device therein so that the primary receiver unit 104 is configured to administer insulin (or other appropriate drug) therapy to patients, for example, for administering and modifying basal profiles, as well as for determining appropriate boluses for administration based on, among others, the detected analyte levels received from the data processing unit 102. An infusion device may be an external device or an internal device (wholly implantable in a user).

In particular embodiments, the data processing terminal 105, which may include an insulin pump, may be configured to receive the analyte signals from the data processing unit 102, and thus, incorporate the functions of the primary receiver unit 104 including data processing for managing the patient's insulin therapy and analyte monitoring. In certain embodiments, the communication link 103 as well as one or more of the other communication interfaces shown in FIG. 1 may use one or more of an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements) while avoiding potential data collision and interference.

Figure 2:
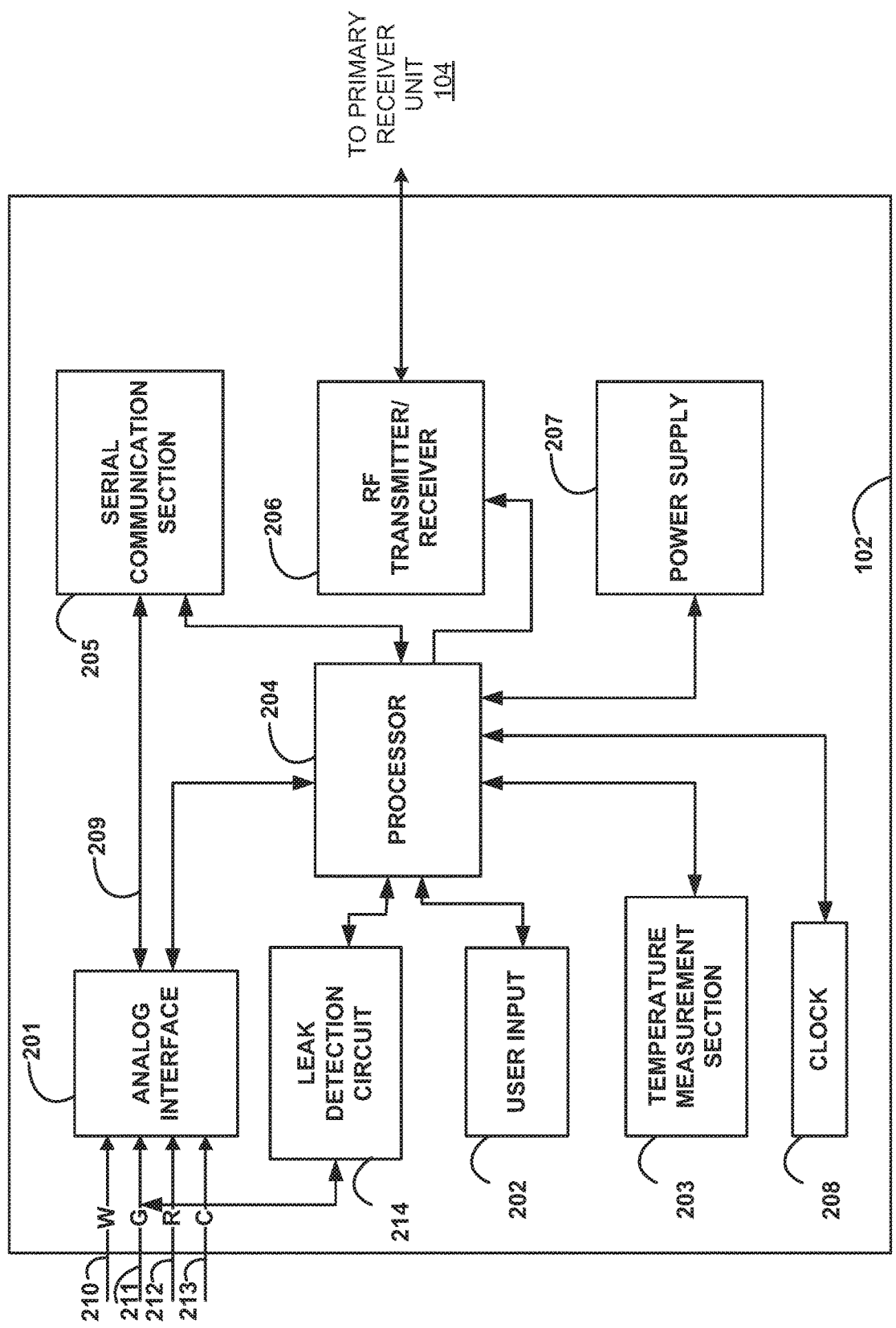
FIG. 2 shows a block diagram of an embodiment of the transmitter unit of the data monitoring and management system of FIG. 1.

FIG. 2 is a block diagram of the data processing unit of the data monitoring and detection system shown in FIG. 1 in accordance with certain embodiments. The data processing unit 102 thus may include one or more of an analog interface 201 configured to communicate with the sensor 101 (FIG. 1), a user input 202, and a temperature detection section 203, each of which is operatively coupled to a transmitter processor 204 such as a central processing unit (CPU). The transmitter may include user input and/or interface components or may be free of user input and/or interface components.

Further shown in FIG. 2 are serial communication section 205 and an RF transmitter 206, each of which is also operatively coupled to the transmitter processor 204. Moreover, a power supply 207, such as a battery, may also be provided in the data processing unit 102 to provide the necessary power for the data processing unit 102. Additionally, as can be seen from the Figure, clock 208 may be provided to, among others, supply real time information to the transmitter processor 204.

As can be seen in the embodiment of FIG. 2, the sensor 101 (FIG. 1) includes four contacts, three of which are electrodes—work electrode (W) 210, guard contact (G) 211, reference electrode (R) 212, and counter electrode (C) 213, each operatively coupled to the analog interface 201 of the data processing unit 102. Analog interface 201 is further coupled to serial communication section 205 via coupling connection 209. In certain embodiments, each of the work electrode (W) 210, guard contact (G) 211, reference electrode (R) 212, and counter electrode (C) 213 may be made using a conductive material that may be applied by, e.g., chemical vapor deposition (CVD), physical vapor deposition, sputtering, reactive sputtering, printing, coating, ablating (e.g., laser ablation), painting, dip coating, etching, and the like. Materials include but are not limited to aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

The processor 204 may be configured to generate and/or process control signals to the various sections of the data processing unit 102 during the operation of the data processing unit 102. In certain embodiments, the processor 204 also includes memory (not shown) for storing data such as the identification information for the data processing unit 102, as well as the data associated with signals received from the sensor 101. The stored information may be retrieved and processed for transmission to the primary receiver unit 104 under the control of the processor 204. Furthermore, the power supply 207 may include a commercially available battery.

In certain embodiments, a manufacturing process of the data processing unit 102 may place the data processing unit 102 in the lower power, non-operating state (i.e., post-manufacture sleep mode). In this manner, the shelf life of the data processing unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present disclosure, the power supply unit 207 is configured to provide the necessary power to each of the components of the data processing unit 102 shown in FIG. 2.

Referring back to FIG. 2, the power supply section 207 of the data processing unit 102 in one embodiment may include a rechargeable battery unit that may be recharged by a separate power supply recharging unit (for example, provided in the receiver unit 104) so that the data processing unit 102 may be powered for a longer period of usage time. In certain embodiments, the data processing unit 102 may be configured without a battery in the power supply section 207, in which case the data processing unit 102 may be configured to receive power from an external power supply source (for example, a battery, electrical outlet, etc.) as discussed in further detail below.

Referring yet again to FIG. 2, a temperature detection section 203 of the data processing unit 102 is configured to monitor the temperature of the skin near the sensor insertion site. The temperature reading may be used to adjust the analyte readings obtained from the analog interface 201. Also shown is a leak detection circuit 214 coupled to the guard contact (G) 211 and the processor 204 in the data processing unit 102 of the data monitoring and management system 100. The leak detection circuit 214 may be configured to detect leakage current in the sensor 101 to determine whether the measured sensor data is corrupt or whether the measured data from the sensor 101 is accurate. Such detection may trigger a notification to the user.

Figure 3:
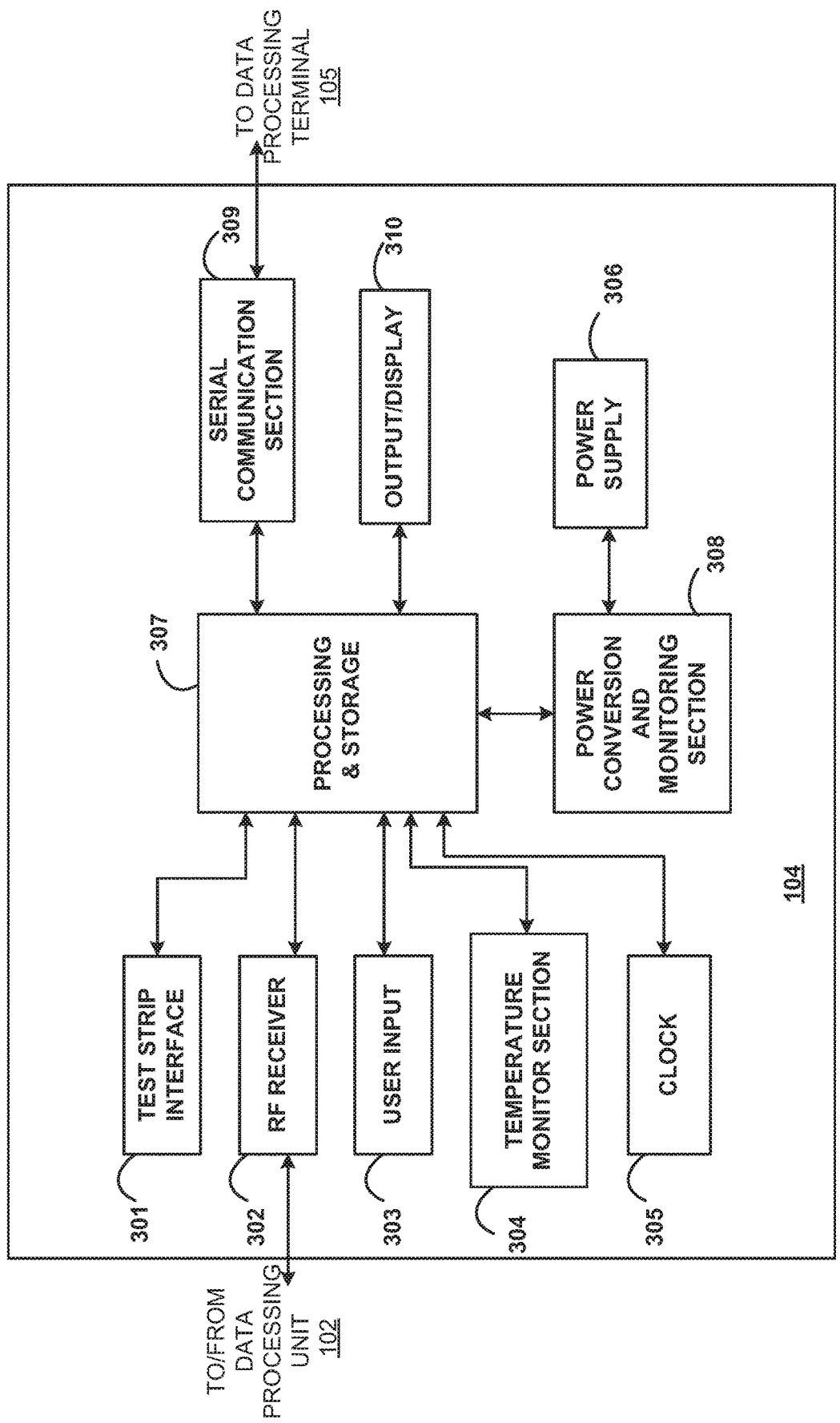
FIG. 3 shows a block diagram of an embodiment of the receiver/monitor unit of the data monitoring and management system of FIG. 1.

FIG. 3 is a block diagram of the receiver/monitor unit such as the primary receiver unit 104 of the data monitoring and management system shown in FIG. 1 in accordance with certain embodiments. The primary receiver unit 104 includes one or more of: a blood glucose test strip interface 301, an RF receiver 302, an input 303, a temperature detection section 304, and a clock 305, each of which is operatively coupled to a processing and storage section 307. The primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the processing and storage unit 307. The receiver may include user input and/or interface components or may be free of user input and/or interface components.

In certain embodiments, the test strip interface 301 includes a glucose level testing portion to receive a blood (or other body fluid sample) glucose test or information related thereto. For example, the interface may include a test strip port to receive a glucose test strip. The device may determine the glucose level of the test strip, and optionally display (or otherwise notice) the glucose level on the output 310 of the primary receiver unit 104. Any suitable test strip may be employed, e.g., test strips that only require a very small amount (e.g., one microliter or less, e.g., 0.5 microliter or less, e.g., 0.1 microliter or less), of applied sample to the strip in order to obtain accurate glucose information, e.g.

FreeStyle® blood glucose test strips from Abbott Diabetes Care, Inc. Glucose information obtained by the in vitro glucose testing device may be used for a variety of purposes, computations, etc. For example, the information may be used to calibrate sensor 101, confirm results of the sensor 101 to increase the confidence thereof (e.g., in instances in which information obtained by sensor 101 is employed in therapy related decisions), etc.

In one aspect, the RF receiver 302 is configured to communicate, via the communication link 103 (FIG. 1) with the RF transmitter 206 of the data processing unit 102, to receive encoded data from the data processing unit 102 for, among others, signal mixing, demodulation, and other data processing. The input 303 of the primary receiver unit 104 is configured to allow the user to enter information into the primary receiver unit 104 as needed. In one aspect, the input 303 may include keys of a keypad, a touch-sensitive screen, and/or a voice-activated input command unit, and the like. The temperature monitor section 304 may be configured to provide temperature information of the primary receiver unit 104 to the processing and control section 307, while the clock 305 provides, among others, real time or clock information to the processing and storage section 307.

Each of the various components of the primary receiver unit 104 shown in FIG. 3 is powered by the power supply 306 (or other power supply) which, in certain embodiments, includes a battery. Furthermore, the power conversion and monitoring section 308 is configured to monitor the power usage by the various components in the primary receiver unit 104 for effective power management and may alert the user, for example, in the event of power usage which renders the primary receiver unit 104 in sub-optimal operating conditions. The serial communication section 309 in the primary receiver unit 104 is configured to provide a bi-directional communication path from the testing and/or manufacturing equipment for, among others, initialization, testing, and configuration of the primary receiver unit 104. Serial communication section 309 can also be used to upload data to a computer, such as time-stamped blood glucose data. The communication link with an external device (not shown) can be made, for example, by cable (such as USB or serial cable), infrared (IR) or RF link. The output/display 310 of the primary receiver unit 104 is configured to provide, among others, a graphical user interface (GUI), and may include a liquid crystal display (LCD) for displaying information. Additionally, the output/display 310 may also include an integrated speaker for outputting audible signals as well as to provide vibration output as commonly found in handheld electronic devices, such as mobile telephones, pagers, etc. In certain embodiments, the primary receiver unit 104 also includes an electro-luminescent lamp configured to provide backlighting to the output 310 for output visual display in dark ambient surroundings.

Referring back to FIG. 3, the primary receiver unit 104 may also include a storage section such as a programmable, non-volatile memory device as part of the processor 307, or provided separately in the primary receiver unit 104, operatively coupled to the processor 307. The processor 307 may be configured to perform Manchester decoding (or other protocol(s)) as well as error detection and correction upon the encoded data received from the data processing unit 102 via the communication link 103.

In further embodiments, the data processing unit 102 and/or the primary receiver unit 104 and/or the secondary receiver unit 106, and/or the data processing terminal/infusion section 105 may be configured to receive the blood glucose value wirelessly over a communication link from, for example, a blood glucose meter. In further embodiments, a user manipulating or using the analyte monitoring system 100 (FIG. 1) may manually input the blood glucose value using, for example, a user interface (for example, a keyboard, keypad, voice commands, and the like) incorporated in the one or more of the data processing unit 102, the primary receiver unit 104, secondary receiver unit 106, or the data processing terminal/infusion section 105.

Additional detailed descriptions of embodiments of the continuous analyte monitoring system, embodiments of its various components are provided in U.S. Pat. No. 6,175,752 issued Jan. 16, 2001 entitled "Analyte Monitoring Device and Methods of Use", and in application Ser. No. 10/745,878 filed Dec. 26, 2003, now U.S. Pat. No. 7,811,231, entitled "Continuous Glucose Monitoring System and Methods of Use", each assigned to the Assignee of the present application, and the disclosures of each of which are incorporated herein by reference for all purposes.

FIG. 4 schematically shows an embodiment of an analyte sensor in accordance with the present disclosure. The sensor 400 includes electrodes 401, 402 and 403 on a base 404. The sensor may be wholly implantable in a user or may be configured so that only a portion is positioned within (internal) a user and another portion outside (external) a user. For example, the sensor 400 may include a portion positionable above a surface of the skin 410, and a portion positioned below the skin. In such embodiments, the external portion may include contacts (connected to respective electrodes of the second portion by traces) to connect to another device also external to the user such as a transmitter unit. While the embodiment of FIG. 4 shows three electrodes side-by-side on the same surface of base 404, other configurations are contemplated, e.g., fewer or greater electrodes, some or all electrodes on different surfaces of the base or present on another base, some or all electrodes stacked together, electrodes of differing materials and dimensions, etc.

FIG. 5A shows a perspective view of an embodiment of an electrochemical analyte sensor 500 having a first portion (which in this embodiment may be characterized as a major portion) positionable above a surface of the skin 510, and a second portion (which in this embodiment may be characterized as a minor portion) that includes an insertion tip 530 positionable below the skin, e.g., penetrating through the skin and into, e.g., the subcutaneous space 520, in contact with the user's biofluid such as interstitial fluid. Contact portions of a working electrode 501, a reference electrode 502, and a counter electrode 503 are positioned on the portion of the sensor 500 situated above the skin surface 510. Working electrode 501, a reference electrode 502, and a counter electrode 503 are shown at the second section and particularly at the insertion tip 530. Traces may be provided from the electrode at the tip to the contact, as shown in FIG. 5A. It is to be understood that greater or fewer electrodes may be provided on a sensor. For example, a sensor may include more than one working electrode and/or the counter and reference electrodes may be a single counter/reference electrode, etc.

FIG. 5B shows a cross sectional view of a portion of the sensor 500 of FIG. 5A. The electrodes 501, 502 and 503, of the sensor 500 as well as the substrate and the dielectric layers are provided in a layered configuration or construction. For example, as shown in FIG. 5B, in one aspect, the sensor 500 (such as the sensor 101 FIG. 1), includes a substrate layer 504, and a first conducting layer 501 such as carbon, gold, etc., disposed on at least a portion of the substrate layer 504, and which may provide the working electrode. Also shown disposed on at least a portion of the first conducting layer 501 is a sensing layer 508.

Referring back to FIG. 5B, a first insulation layer such as a first dielectric layer 505 is disposed or layered on at least a portion of the first conducting layer 501, and further, a second conducting layer 509 may be disposed or stacked on top of at least a portion of the first insulation layer (or dielectric layer) 505. As shown in FIG. 5B, the second conducting layer 509 may provide the reference electrode 502, and in one aspect, may include a layer of silver/silver chloride (Ag/AgCl), gold, etc.

Referring still again to FIG. 5B, a second insulation layer 506 such as a dielectric layer in one embodiment may be disposed or layered on at least a portion of the second conducting layer 509. Further, a third conducting layer 503 may provide the counter electrode 503. It may be disposed on at least a portion of the second insulation layer 506. Finally, a third insulation layer 507 may be disposed or layered on at least a portion of the third conducting layer 503. In this manner, the sensor 500 may be layered such that at least a portion of each of the conducting layers is separated by a respective insulation layer (for example, a dielectric layer).

The embodiment of FIGS. 5A and 5B show the layers having different lengths. Some or all of the layers may have the same or different lengths and/or widths.

In certain embodiments, some or all of the electrodes 501, 502, 503 may be provided on the same side of the substrate 504 in the layered construction as described above, or alternatively, may be provided in a co-planar manner such that two or more electrodes may be positioned on the same plane (e.g., side-by side (e.g., parallel) or angled relative to each other) on the substrate 504. For example, co-planar electrodes may include a suitable spacing there between and/or include dielectric material or insulation material disposed between the conducting layers/electrodes. Furthermore, in certain embodiments one or more of the electrodes 501, 502, 503 may be disposed on opposing sides of the substrate 504. In such embodiments, contact pads may be on the same or different sides of the substrate. For example, an electrode may be on a first side and its respective contact may be on a second side, e.g., a trace connecting the electrode and the contact may traverse through the substrate.

In certain embodiments, the data processing unit 102 may be configured to perform sensor insertion detection and data quality analysis, information pertaining to which may also be transmitted to the primary receiver unit 104 periodically at the predetermined time interval. In turn, the receiver unit 104 may be configured to perform, for example, skin temperature compensation/correction as well as calibration of the sensor data received from the data processing unit 102.

As noted above, analyte sensors may include an analyte-responsive enzyme in a sensing layer. Some analytes, such as oxygen, can be directly electrooxidized or electroreduced on a sensor, and more specifically at least on a working electrode of a sensor. Other analytes, such as glucose and lactate, require the presence of at least one electron transfer agent and/or at least one catalyst to facilitate the electrooxidation or electroreduction of the analyte. Catalysts may also be used for those analytes, such as oxygen, that can be directly electrooxidized or electroreduced on the working electrode. For these analytes, each working electrode includes a sensing layer (see for example sensing layer 508 of FIG. 5B) formed proximate to or on a surface of a working electrode. In many embodiments, a sensing layer is formed near or on only a small portion of at least a working electrode.

A variety of different sensing layer configurations may be used. In certain embodiments, the sensing layer is deposited on the conductive material of a working electrode. The sensing layer may extend beyond the conductive material of the working electrode. In some cases, the sensing layer may also extend over other electrodes, e.g., over the counter electrode and/or reference electrode (or counter/reference is provided). The sensing layer may be integral with the material of an electrode.

A sensing layer that is in direct contact with the working electrode may contain an electron transfer agent to transfer electrons directly or indirectly between the analyte and the working electrode, and/or a catalyst to facilitate a reaction of the analyte.

A sensing layer that is not in direct contact with the working electrode may include a catalyst that facilitates a reaction of the analyte. However, such sensing layers may not include an electron transfer agent that transfers electrons directly from the working electrode to the analyte, as the sensing layer is spaced apart from the working electrode. One example of this type of sensor is a glucose or lactate sensor which includes an enzyme (e.g., glucose oxidase, glucose dehydrogenase, lactate oxidase, and the like) in the sensing layer. The glucose or lactate may react with a second compound in the presence of the enzyme. The second compound may then be electrooxidized or electroreduced at the electrode. Changes in the signal at the electrode indicate changes in the level of the second compound in the fluid and are proportional to changes in glucose or lactate level and, thus, correlate to the analyte level.

In certain embodiments which include more than one working electrode, one or more of the working electrodes do not have a corresponding sensing layer, or have a sensing layer which does not contain one or more components (e.g., an electron transfer agent and/or catalyst) needed to electrolyze the analyte. Thus, the signal at this working electrode corresponds to background signal which may be removed from the analyte signal obtained from one or more other working electrodes that are associated with fully-functional sensing layers by, for example, subtracting the signal.

In certain embodiments, the sensing layer includes one or more electron transfer agents. Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic or organometallic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

One type of polymeric electron transfer agent contains a redox species covalently bound in a polymeric composition. An example of this type of mediator is poly(vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation. Another example of an ionically-bound mediator is a positively charged polymer such as quaternized poly(4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, or derivatives thereof. The electron transfer agents may also have one or more ligands covalently bound in a polymer, each ligand having at least one nitrogen-containing heterocycle, such as pyridine, imidazole, or derivatives thereof. The present disclosure may employ electron transfer agents having a redox potential ranging from about −100 mV to about +150 mV versus the standard calomel electrode (SCE), e.g., ranges from about −100 mV to about +150 mV, e.g., ranges from about −50 mV to about +50 mV, e.g., electron transfer agents have osmium redox centers and a redox potential ranging from +50 mV to −150 mV versus SCE.

The sensing layer may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, such as a glucose oxidase, glucose dehydrogenase (e.g., pyrroloquinoline quinone glucose dehydrogenase (PQQ)), or oligosaccharide dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent (which, as described above, may be polymeric). A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

Certain embodiments include a Wired Enzyme™ sensing layer that works at a gentle oxidizing potential, e.g., a potential of about +40 mV. This sensing layer uses an osmium (Os)-based mediator designed for low potential operation and is stably anchored in a polymeric layer. Accordingly, in certain embodiments the sensing element is a redox active component that includes (1) Osmium-based mediator molecules attached by stable (bidente) ligands anchored to a polymeric backbone, and (2) glucose oxidase enzyme molecules. These two constituents are crosslinked together.

A mass transport limiting layer (not shown), e.g., an analyte flux modulating layer, may be included with the sensor to act as a diffusion-limiting barrier to reduce the rate of mass transport of the analyte, for example, glucose or lactate, into the region around the working electrodes. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may serve many functions, e.g., functionalities of a biocompatible layer and/or interferent-eliminating layer may be provided by the mass transport limiting layer.

In certain embodiments, a mass transport limiting layer is a membrane composed of crosslinked polymers containing heterocyclic nitrogen groups, such as polymers of polyvinylpyridine and polyvinylimidazole. Electrochemical sensors equipped with such membranes have considerable sensitivity and stability, and a large signal-to-noise ratio, in a variety of conditions.

According to certain embodiments, a membrane is formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. Optionally, hydrophilic or hydrophobic modifiers may be used to "fine-tune" the permeability of the resulting membrane to an analyte of interest. Optional hydrophilic modifiers, such as poly(ethylene glycol), hydroxyl or polyhydroxyl modifiers, may be used to enhance the biocompatibility of the polymer or the resulting membrane.

A biocompatible layer (not shown) may be provided over at least that portion of the sensor which is subcutaneously inserted into the patient. The biocompatible layer may be incorporated in the interferent-eliminating layer or in the mass transport limiting layer or may be a separate layer. The layer may prevent the penetration of large biomolecules into the electrodes. The biocompatible layer may also prevent protein adhesion to the sensor, formation of blood clots, and other undesirable interactions between the sensor and body. For example, a sensor may be completely or partially covered on its exterior with a biocompatible coating.

An interferent-eliminating layer (not shown) may be included in the sensor. The interferent-eliminating layer may be incorporated in the biocompatible layer or in the mass transport limiting layer or may be a separate layer. Interferents are molecules or other species that are electroreduced or electrooxidized at the electrode, either directly or via an electron transfer agent, to produce a false signal. In one embodiment, a film or membrane prevents the penetration of one or more interferents into the region around the working electrode. In many embodiments, this type of interferent-eliminating layer is much less permeable to one or more of the interferents than to the analyte. An interferent-eliminating layer may include ionic components to reduce the permeability of the interferent-eliminating layer to ionic interferents having the same charge as the ionic components. Another example of an interferent-eliminating layer includes a catalyst for catalyzing a reaction which removes interferents.

A sensor may also include an active agent such as an anticlotting and/or antiglycolytic agent(s) disposed on at least a portion a sensor that is positioned in a user. An anticlotting agent may reduce or eliminate the clotting of blood or other body fluid around the sensor, particularly after insertion of the sensor. Blood clots may foul the sensor or irreproducibly reduce the amount of analyte which diffuses into the sensor. Examples of useful anticlotting agents include heparin and tissue plasminogen activator (TPA), as well as other known anticlotting agents. Embodiments may include an antiglycolytic agent or precursor thereof. The term "antiglycolytic" is used broadly herein to include any substance that at least retards glucose consumption of living cells.

Sensors described herein may be configured to require no system calibration or no user calibration. For example, a sensor may be factory calibrated and need not require further calibrating. In certain embodiments, calibration may be required, but may be done without user intervention, i.e., may be automatic. In those embodiments in which calibration by the user is required, the calibration may be according to a predetermined schedule or may be dynamic, i.e., the time for which may be determined by the system on a real-time basis according to various factors. Calibration may be accomplished using an in vitro test strip or other calibrator, e.g., a small sample test strip such as a test strip that requires less than about 1 microliter of sample (for example FreeStyle® blood glucose monitoring test strips from Abbott Diabetes Care). For example, test strips that require less than about 1 nanoliter of sample may be used. In certain embodiments, a sensor may be calibrated using only one sample of body fluid per calibration event. For example, a user need only lance a body part one time to obtain sample for a calibration event (e.g., for a test strip), or may lance more than one time within a short period of time if an insufficient volume of sample is obtained firstly. Embodiments include obtaining and using multiple samples of body fluid for a given calibration event, where glucose values of each sample are substantially similar. Data obtained from a given calibration event may be used independently to calibrate or combined with data obtained from previous calibration events, e.g., averaged including weighted averaged, filtered and the like, to calibrate.

An analyte system may include an optional alarm system that, e.g., based on information from a processor, warns the patient of a potentially detrimental condition of the analyte. For example, if glucose is the analyte, an alarm system may warn a user of conditions such as hypoglycemia and/or hyperglycemia and/or impending hypoglycemia, and/or impending hyperglycemia. An alarm system may be triggered when analyte levels reach or exceed a threshold value. An alarm system may also, or alternatively, be activated when the rate of change or acceleration of the rate of change in analyte level increase or decrease, reaches or exceeds a threshold rate or acceleration. For example, in the case of a glucose monitoring system, an alarm system may be activated if the rate of change in glucose concentration exceeds a threshold value which might indicate that a hyperglycemic or hypoglycemic condition is likely to occur. A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

The subject disclosure also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a transmitter, a receiver/display unit, and a drug administration system. In some cases, some or all components may be integrated in a single unit. The sensor-based drug delivery system may use data from the one or more sensors to provide necessary input for a control algorithm/mechanism to adjust the administration of drugs, e.g., automatically or semi-automatically. As an example, a glucose sensor could be used to control and adjust the administration of insulin from an external or implanted insulin pump.

As discussed in further detail below, in accordance with aspects of the present disclosure an offset based model for improving the accuracy of the analyte sensor signals to address abnormal sensor sensitivity event including, for example, early signal (sensitivity) attenuation is provided. More specifically, in accordance with aspects of the present disclosure, when an analyte sensor is experiencing signal attenuation, it is assumed that the associated sensor sensitivity remains constant, and rather, a predetermined signal offset results. Accordingly, determination of the offset and applying the determined offset to analyte sensor signals provide improved accuracy in the monitored analyte levels from the sensor, even in the case where the analyte sensor is experiencing an abnormal sensitivity event such as, for example, early signal attenuation.

In this manner, in one aspect, there is provided a procedure to retrospectively (or in real time) determine a glucose estimate based on sensor signals and available reference measurements from, for example, in vitro testing that maximizes both the optimal accuracy and precision, while minimally susceptible to errors that may be caused by outlier reference value and/or momentary sensor signal degradation sources such as early signal attenuation.

In providing the best glucose estimate, it is found that the simplest transformation from a raw sensor current signal in arbitrary hardware units to a glucose signal in proper glucose concentration units is in fact a linear scaling operation without any offset. The scaling factor is commonly called sensitivity, in which a raw sensor current signal can be translated into glucose concentration units by dividing the signal's value by the sensitivity value. As a result, the nominal aspect of calibration involves using a reasonable amount of information to infer the most accurate and precise estimate of sensitivity.

While this is the case under normal operating conditions, there are several exceptions in which the sensor response to the analyte may be contaminated by other artifacts. An example is during the presence of early signal attenuation (ESA) condition, where, suppose the sensor has been properly calibrated using its true sensitivity, the resulting glucose values are lower than that determined by other means or an identical sensor that is not subject to ESA condition.

In such non-normal operating conditions, the best glucose estimate from the sensor may be determined by retaining the same best estimate of sensitivity as in the nominal case, and in addition, determining the best estimate of a slowly time varying offset. This may be defined as the offset based model. In one aspect, the offset based model assumes that the true gain or sensitivity of the system remains the same throughout the sensor's life, and that non-normal operating conditions such as ESA condition is best represented by a nonzero, slowly time varying offset.

Figure 6:
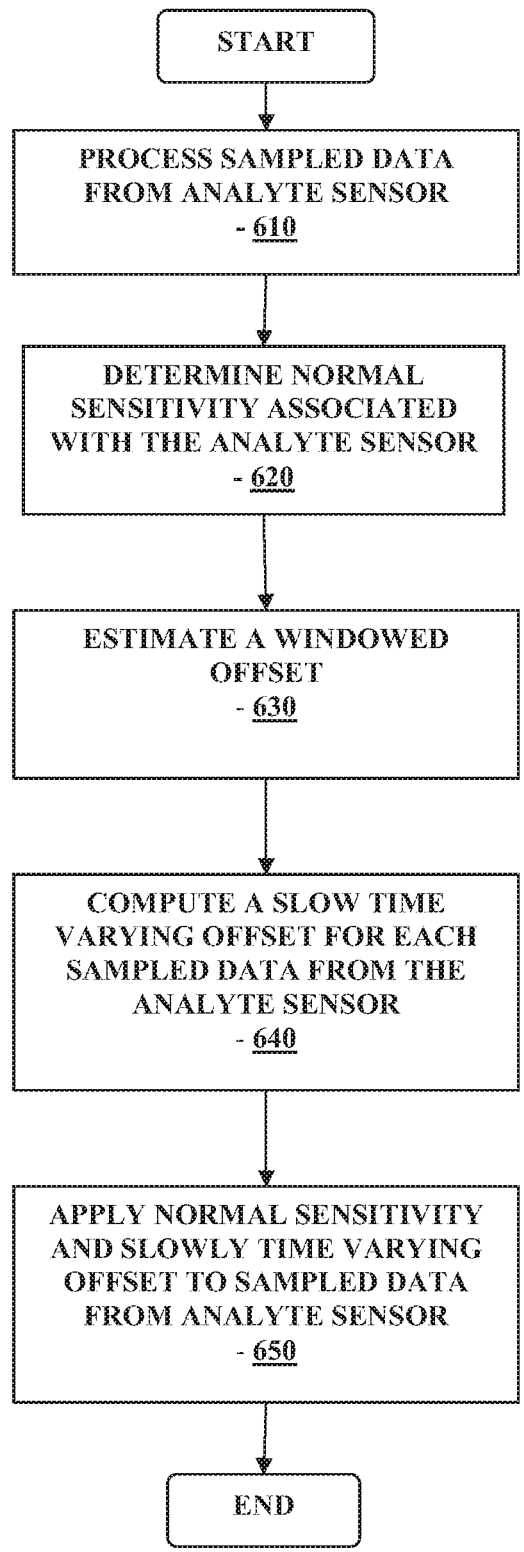
FIG. 6 is a flowchart illustrating the offset model based analyte sensor data calibration in accordance with one aspect of the present disclosure.

Referring now to the Figures, FIG. 6 is a flowchart illustrating the offset model based analyte sensor data calibration in accordance with one aspect of the present disclosure. In one aspect, sampled data from an analyte sensor is processed (610). For example, in one embodiment, the raw signal (such as raw current signal) received from the analyte sensor is retrospectively lag corrected, and/or filtered or smoothed in addition to temperature corrected or compensated. Thereafter, a normal sensitivity associated with the analyte sensor is determined (620) as described in further detail below in conjunction with FIG. 7.

Referring again to FIG. 6, a windowed offset is thereafter estimated using each available paired points (of sensor data and time corresponding reference blood glucose measurement, for example) within a valid window (630). As discussed above, the effective sensitivity associated with the analyte sensor is, in one embodiment, held constant at the determined normal sensitivity discussed above. Using this normal sensitivity Sn, each pairable sensor signal is scaled into glucose concentrations. For purpose of signal pairing, the sensor signal Gr can either be the raw signal itself, lag corrected, and/or filtered or smoothed in addition to temperature corrected or compensated. The scaled value Gs at any time k is then described as follows:

$$Gs(k)=Gr(k)/Sn$$

where Sn is the normal sensitivity previously computed. For each pairable scaled sensor signal Gs and reference blood glucose measurement (BG) in a window, a difference (DGs) may be determined as follows:

$$DGs(k)=Gs(k)-BG(k)$$

where k denotes the time index of a pair.

The difference value (DGs) between each pairable scaled sensor signal Gs to its corresponding reference blood glucose (BG) measurement pair is a reflection of the latest offset. In one aspect, the plurality of these computed offset within this window of reference blood glucose measurement—sensor pairs determine the windowed offset in this window. An example of obtaining a windowed offset using the available data in a window is averaging the difference value (DGs). Yet another example is to take the median value of the difference value (DGs). Under normal operating conditions, the windowed offset is zero.

Referring still again to FIG. 6, thereafter, the estimated offset may be used to obtain a slowly time varying offset Go(k) at every minute k (640). For a retrospective application, interpolating offset values obtained around clusters of reference blood glucose measurement—sensor pairs may be used in place of a slowly time varying offset Go(k). For a real-time application, prior knowledge of how offsets change over time given other known circumstances or parameters may be used to determine a slowly time varying offset Go(k). For example, when ESA condition is suspected, a time evolution of the offset based on the available offset data may be inferred by fitting the offset data to an ESA offset model whose architecture may have been determined a priori.

Finally, for each one minute sampled analyte data (or any other periodically sampled analyte data from the sensor), the slowly time varying estimated offset Go(k) and the best estimate of the constant Sn are applied to the sampled analyte data to estimate the corresponding glucose value (650). That is, for example, for each of the one minute sampled analyte sensor data Gr(k) which has been lag corrected, temperature compensated, and/or smoothed or filtered, the slowly time varying offset Go(k) is applied with the previously determined normal sensitivity Sn to determine the corresponding estimated glucose value Gf(k) based on the following relationship:

$$Gf(k)=[Gr(k)/Sn]-Go(k)$$

Figure 7:
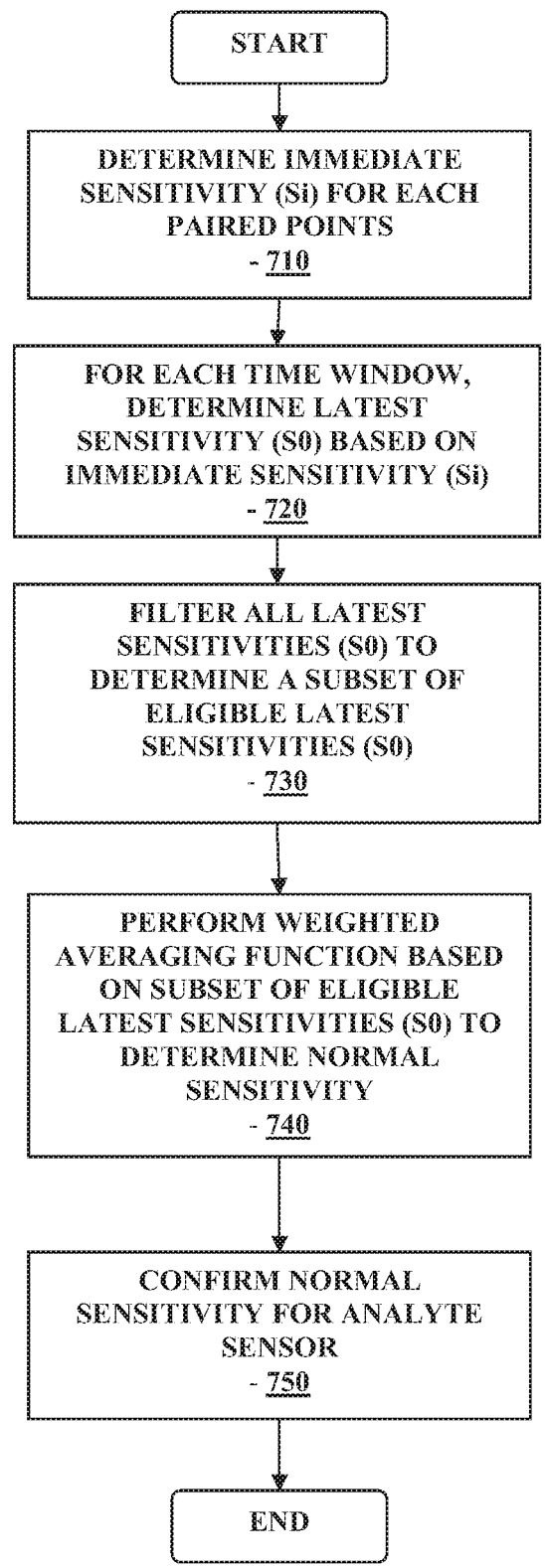
FIG. 7 is a flowchart illustrating the normal sensitivity determination routine of FIG. 6 associated with the analyte sensor in accordance with one embodiment of the present disclosure.

FIG. 7 is a flowchart illustrating the normal sensitivity Sn determination routine of FIG. 6 associated with the analyte sensor with one embodiment of the present disclosure. Referring to the Figure, to determine the normal sensitivity associated with the analyte sensor (620) (FIG. 6), given the available paired data points of analyte sensor signals and the time corresponding reference measurements (for example, the in vitro blood glucose measurements taken, for example, at given time intervals (periodic or otherwise)), the immediate sensitivity (Si) for each paired data points are determined (710). That is, in one embodiment, for each paired sensor data and reference blood glucose measurement, the sensor data is lag corrected and smoothed or filtered, based on a nominal time constant (for example, 10 minutes or any other suitable time period), and a ratio of the lag corrected and smoothed data Gr(k) over the reference blood glucose measurement BG is taken to determine the corresponding immediate sensitivity (Si).

$$Si(k)=Gr(k)/BG$$

Referring back to FIG. 7, with the determined immediate sensitivity (Si), for each time window (which may be preset or variable), the latest sensitivity (S0) associated with the analyte sensor is estimated based on the determined immediate sensitivity (Si) values within that time window (720). That is, a time window such as, for example, a five hour window (or any other suitable time window) is defined with a center that shifts or advances through the sensor's life (as a measure of time) in an increment of, for example, one hour. Thereafter, within the time window, the determined immediate sensitivity (Si) is collected as well as the associated rate of change of the sensor signals.

In one embodiment, a least squares fit line is calculated for the sensor rate of change as a function of the corresponding immediate sensitivity (Si) within the time window. The vertical difference between each immediate sensitivity (Si) and the calculated least squares fit line corresponds to a lag residual compensated sensitivity. Furthermore, the intercept at the zero rate of change of this least squares fit line corresponds to the estimate of the latest sensitivity (S0) in the corresponding time window.

It is to be noted that the standard error associated with the least squares fit line may correspond to how the available data fits the lag correction model as well as how much variance is introduced from the zero mean sensitivity error sources. In this context, the zero mean sensitivity error sources are factors that could increase the variance of the sensitivity calculation error without significantly biasing the result in any direction. Examples of such zero mean sensitivity error sources include random sensor error and/or noise, random reference blood glucose error, and insufficient lag correction. Insufficient lag correction may result from using a time constant that is smaller or larger than the actual value, or from using a model that is not sufficiently robust to capture all the transient behavior between blood glucose levels to interstitial glucose levels.

Also, referring back to FIG. 7, using the available lag residual compensated sensitivity values, along with their associated timestamps, in one embodiment, the least squares fit line may be determined based on time as a function of the lag residual compensated sensitivity values to estimate the sensitivity rate of change for each time window. In this manner, as discussed above, for each time window, the latest sensitivity (S0) based on the determined immediate sensitivity (Si) is calculated. Referring still to FIG. 7, given the multiple time windows, a subset of the time windows are selected based on the determined latest sensitivity, the immediate sensitivity (Si) as well as the lag residual compensated sensitivity values. In this manner, in one aspect, the latest sensitivity values (S0) that are taken during non-normal operation modes such as during ESA condition are discounted. In these cases, the latest sensitivity values (S0) tend to be lower than the true/accurate value. For example, in one embodiment, the time windows are selected for latest sensitivity values (S0) that are in the upper $50^{th}$ percentile of the entire time window population.

Also, the subset of time windows are additionally identified for those with a suitable or sufficient least squares fit line of the sensor rate of change versus immediate sensitivity (Si). The better the fit, the more likely a given window will produce a reliable latest sensitivity value (S0). In one embodiment, the latest sensitivity values (S0) retained are those where the standard sensitivity error (Sse) based on the determined least squares fit line in the lower quartile of the entire time window population.

Additionally, the subset of time windows may further be narrowed to those associated with a relatively low immediate sensitivity (Si) rate of change value. A window with a relatively high immediate sensitivity (Si) rate of change value may indicate a region of poor sensor stability, or a consistent bias in the reference blood glucose values due to unknown circumstances. For example, in one embodiment, only latest sensitivity values (S0) whose rate of change magnitude is in the lower quartile of the entire time window population may be retained. Referring still to FIG. 7, based on the one or more criteria described above, the subset of eligible latest sensitivities (S0) are filtered or identified from all latest sensitivity values (S0) (730). It is to be noted that the threshold for inclusion within the subset of time windows may be varied and include other thresholds or criteria including, for example, selecting those time windows associated with the latest sensitivity in the upper $75^{th}$ percentile of the entire population (or some other suitable threshold), selecting those time windows associated with preferred elapsed time ranges since the start of a sensor insertion, or selecting those time windows associated with preferred ranges of times of days. Indeed, the numerical examples described herein are intended to provide exemplary embodiments and the scope of the present disclosure is not in any manner intended to be limited to such examples.

Referring back to FIG. 7, as shown, weighted averaging function is applied to the subset of eligible latest sensitivity values (S0) to determine the estimate of the normal sensitivity (740). For example, in one embodiment, each latest sensitivity value (S0) may be weighted by $(1/Sse)^2$. In another embodiment, each latest sensitivity value (S0) may be weighted by $(S0/(Sse)^2)$. In yet another embodiment, other measures of fit such as the absolute value of immediate sensitivity (Si) rate of change of each window can be included into the weighting.

Thereafter, the estimated normal sensitivity determined is confirmed by, for example, comparing it to the median sensitivity computed from all eligible latest sensitivity values (S0) and ensuring that the estimated normal sensitivity is no smaller than the median sensitivity (750). Since numerical determination may incur a certain degree of uncertainty, it is possible that the normal sensitivity candidate may be lower than some clusters of latest sensitivity values (S0) that may be a better candidate for the normal sensitivity estimate. As long as the bottom end of the uncertainty of the latest sensitivity values (S0) is still below the candidate normal sensitivity value, no adjustment may be needed. Otherwise, the normal sensitivity may be adjusted further up to that bottom end limit. An example of computing the bottom end of latest sensitivity values (S0) may include subtracting each latest sensitivity value (S0) with three times (or any other suitable factor) the corresponding standard error (Sse) value. When the mean of this lower bound is higher than the candidate normal sensitivity value, the normal sensitivity should be adjusted to this bound.

In this manner, in accordance with embodiments of the present disclosure, improved real time or retrospective determination of glucose estimate is provided based on analyte sensor data and associated time corresponding reference measurement values (for example, in vitro test results providing associated blood glucose measurements) which improves accuracy and is less prone to abnormal sensor sensitivity events such as, for example, early signal attenuation.

Furthermore, in aspects of the present disclosure, it is contemplated that the highest sustainable in vivo steady state sensitivity associated with an analyte sensor occurs when the sensor is in normal condition. Also, sensitivities determined during reduced or increased mean sensitivity events may be deemed poor or inaccurate representatives of normal sensitivity. Additionally, zero mean sensitivity error sources are not considered to bias the normal sensitivity, and further, lag correction (retrospective or real time) of the analyte sensor raw signal removes most of the rate of change associated sensitivity errors. Moreover, it is considered, in some aspects of the present disclosure, that within a relatively short time window, a single "latest sensitivity" is an accurate representation of the temporal sensitivity—for example, in a five hour time window as in the exemplary discussion set forth above, the "latest sensitivity" may be considered sufficiently representative.

In addition, in a five hour time window, a single effective time constant may be applicable for all available paired points. While different time windows may have different associated time constants, in a steady state condition where other parameters or variables are the same, the time window that has an effective time constant which is closed to an assumed nominal value may have a latest sensitivity value that is more suitable for the normal sensitivity. Finally, in a time window with sufficient number of paired points, the determined sensitivity slope over time may indicate the relative stability of the sensitivity in that time window. As such, again assuming a steady state condition where other parameters or variables are considered to be the same, a time window with a flatter sensitivity slope over time may be a more suitable candidate for the normal sensitivity.

Accordingly, a method in one embodiment includes processing sampled data from analyte sensor, determining a single, fixed, normal sensitivity value associated with the analyte sensor, estimating a windowed offset value associated with the analyte sensor for each available sampled data cluster, computing a time varying offset based on the estimated windowed offset value, and applying the time varying offset and the determined normal sensitivity value to the processed sampled data to estimate an analyte level for the sensor.

Processing the sampled data may include performing retrospective lag correction of the sampled data. Further, processing the sampled data may include smoothing the sampled data from the analyte sensor. In addition, processing the sampled data may include performing temperature correction to the sampled data.

In one aspect, determining the normal sensitivity may include pairing the sampled data from the analyte sensor with one or more time corresponding reference measurement values, where the one or more reference measurement values may include a blood glucose measurement.

A further aspect may include determining an immediate sensitivity value for each paired sampled data and the one or more time corresponding reference measurement values, and also, estimating a latest sensitivity based on the determined immediate sensitivity for each time window.

Yet a further aspect may include defining a subset of the estimated latest sensitivities associated with a subset of the total available time windows corresponding to the respective paired sampled data and the one or more time corresponding reference measurement values.

Additionally, still a further aspect may include weighted averaging the subset of estimated latest sensitivities to determine the normal sensitivity associated with the analyte sensor.

Also, another aspect may include confirming the determined normal sensitivity, where confirming the determined normal sensitivity may include comparing the determined normal sensitivity to a predetermined value, and further, where predetermined value may include a median sensitivity value determined based on the immediate sensitivity associated with each time window.

Also, estimating a windowed offset value in an eligible cluster of data may include collecting one or more pairs of reference measurement value and normal sensitivity adjusted sensor signal to determine the offset of each pair.

The windowed offset value of each pair in a window may be collected to determine a windowed offset value that is most representative of that window.

Additionally, determining a windowed offset value that is most representative of that window may include taking the median of the offset values of each pair in a window, taking the mean of the offset values of each pair in a window, taking a weighted mean of the offset values of each pair in a window, or other means of estimating the most representative offset value given the population of offset values in a window.

Moreover, slowly time varying offset may be determined based on any available windowed offset values using simple interpolation between windowed offset values.

In addition, a slowly time varying offset may be determined by fitting a pre determined mathematical model using any available windowed offset values. One example is a mathematical model similar to the impulse response of a second order model, with the time constants, amplitude, and the start of the response determined by fitting any available windowed offset values.

The estimate of an analyte level for the sensor may be obtained by dividing the latest unscaled value by the normal sensitivity, and then subtracting the result with the latest slowly time varying offset.

An apparatus in accordance with another aspect of the present disclosure includes a data communication interface, one or more processors operatively coupled to the data communication interface and a memory for storing instructions which, when executed by the one or more processors, causes the one or more processors to process sampled data from analyte sensor, determine a single, fixed, normal sensitivity value associated with the analyte sensor, estimate a windowed offset value associated with the analyte sensor for each available sampled data cluster, compute a time varying offset based on the estimated windowed offset value, and apply the time varying offset and the determined normal sensitivity value to the processed sampled data to estimate an analyte level for the sensor.

One or more storage devices having processor readable code embodied thereon, said processor readable code for programming one or more processors to estimate analyte level in accordance with a further aspect of the present disclosure includes processing sampled data from analyte sensor, determining a single, fixed, normal sensitivity value associated with the analyte sensor, estimating a windowed offset value associated with the analyte sensor for each available sampled data cluster, computing a time varying offset based on the estimated windowed offset value, and applying the time varying offset and the determined normal sensitivity value to the processed sampled data to estimate an analyte level for the sensor.

The various processes described above including the processes performed by the data processing unit 102, receiver unit 104/106 or the data processing terminal/infusion section 105 (FIG. 1) in the software application execution environment in the analyte monitoring system 100 including the processes and routines described in conjunction with FIGS. 6-7, may be embodied as computer programs developed using an object oriented language that allows the modeling of complex systems with modular objects to create abstractions that are representative of real world, physical objects and their interrelationships. The software required to carry out the inventive process, which may be stored in the memory or storage device (not shown) of the data processing unit 102, receiver unit 104/106 or the data processing terminal/infusion section 105, may be developed by a person of ordinary skill in the art and may include one or more computer program products.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

What is claimed is:

1. A method of determining a non-attenuated sensitivity of an analyte sensor in fluid contact with interstitial fluid, comprising:
    obtaining, by a data processing unit electrically and communicatively coupled with the analyte sensor, a plurality of data points from signals generated by the analyte sensor, wherein the data processing unit comprises one or more processors, a transceiver to transmit data to a receiving unit, and a memory storing instructions which when executed by the one or more processors enable the data processing unit to perform specified operations;
    pairing, by the data processing unit, the plurality of data points with a reference data to form a plurality of pairs;
    for each pair of the plurality of pairs, determining, by the data processing unit, a corresponding sensor sensitivity at a corresponding time for the pair;
    forming, by the data processing unit, a plurality of time windows each including one or more of the plurality of pairs, so that the plurality of time windows includes the plurality of pairs;
    for each time window, selecting, by the data processing unit, a sensitivity for the analyte sensor from the corresponding sensor sensitivities of the plurality of pairs within the time window to obtain a set of selected sensitivities;
    determining, by the data processing unit, a rate of change of the data points obtained from the analyte sensor for each of the plurality of time windows;
    selecting, by the data processing unit, one or more of the plurality of time windows having a rate of change less than a threshold to obtain a filtered set of selected sensor sensitivities;
    determining, by the data processing unit, a non-attenuated sensitivity based on the filtered set of selected sensor sensitivities;
    applying, by the data processing unit, the determined non-attenuated sensitivity to the plurality of data points obtained from the analyte sensor to estimate an analyte level; and
    causing, by the data processing unit, output of an alarm to a user based on the estimated analyte level.

2. The method of claim 1, wherein the analyte sensor is one of a glucose sensor or a lactate sensor.

3. The method of claim 1, further comprising determining a median sensitivity based on the filtered set of selected sensor sensitivities, and determining that the normal sensitivity is equal to or greater than the median sensitivity.

4. The method of claim 1, further comprising displaying the estimated analyte level on a display device.

5. The method of claim 1, wherein applying the determined non-attenuated sensitivity to the plurality of data points from the analyte sensor to estimate the analyte level comprises applying a time varying offset to the plurality of data points obtained from the analyte sensor.

6. The method of claim 1, wherein the analyte sensor comprises a plurality of electrodes including a working electrode comprising an analyte-responsive enzyme bonded to a polymer disposed on the working electrode.

7. The method of claim 6, wherein the analyte-responsive enzyme is chemically bonded to the polymer.

8. The method of claim 6, wherein the working electrode further comprises a mediator.

9. The method of claim 1, wherein the analyte sensor comprises a plurality of electrodes including a working electrode comprising a mediator bonded to a polymer disposed on the working electrode.

10. The method of claim 9, wherein the mediator is chemically bonded to the polymer.

11. A system, comprising:
    an analyte sensor in fluid contact with interstitial fluid; and
    a receiving device comprising one or more processors, and a memory storing instructions which, when executed by the one or more processors, cause the one or more processors to determine a non-attenuated sensitivity of the analyte sensor, wherein the instruction cause the one or more processors to:
    obtain a plurality of data points from signals generated by the analyte sensor;
    pair the plurality of data points with a reference data to form a plurality of pairs;
    for each pair of the plurality of pairs, determine a corresponding sensor sensitivity at a corresponding time for the pair;
    form a plurality of time windows each including one or more of the plurality of pairs, so that the plurality of time windows includes the plurality of pairs;
    for each time window, select a sensitivity for the analyte sensor from the corresponding sensor sensitivities of the plurality of pairs within the time window to obtain a set of selected sensitivities;

determine a rate of change of the data points obtained from the analyte sensor for each of the plurality of time windows;

select one or more of the plurality of time windows having a rate of change less than a threshold to obtain a filtered set of selected sensor sensitivities;

determine a non-attenuated sensitivity based on the filtered set of selected sensor sensitivities;

apply the determined non-attenuated sensitivity to the plurality of data points obtained from the analyte sensor to estimate an analyte level; and cause output of an alarm to a user based on the estimated analyte level.

12. The system of claim 11, wherein the analyte sensor is one of a glucose sensor or a lactate sensor.

13. The system of claim 11, the memory further storing instructions to determine a median sensitivity based on the filtered set of selected sensor sensitivities, and determine that the normal sensitivity is equal to or greater than the median sensitivity.

14. The system of claim 11, the memory further storing instructions to display the estimated analyte level on a display device.

15. The system of claim 11, the memory storing instructions to apply the determined non-attenuated sensitivity to the plurality of data points from the analyte sensor to estimate the analyte level by at least applying a time varying offset to the plurality of data points obtained from the analyte sensor.

16. The system of claim 11, wherein the analyte sensor comprises a plurality of electrodes including a working electrode comprising an analyte-responsive enzyme bonded to a polymer disposed on the working electrode.

17. The system of claim 16, wherein the analyte-responsive enzyme is chemically bonded to the polymer.

18. The system of claim 16, wherein the working electrode further comprises a mediator.

19. The system of claim 11, wherein the analyte sensor comprises a plurality of electrodes including a working electrode comprising a mediator bonded to a polymer disposed on the working electrode.

20. The system of claim 19, wherein the mediator is chemically bonded to the polymer.

21. The method of claim 1, wherein the estimated analyte level corresponds to a predicted analyte level at a future time, and wherein the alarm is a predictive alarm based on the future time.

22. The method of claim 1, further comprising further comprising comparing the estimated analyte level to a threshold value, wherein the alarm is output in response to the estimated analyte level satisfying the threshold value.

23. The system of claim 11, wherein the estimated analyte level corresponds to a predicted analyte level at a future time, and wherein the alarm is a predictive alarm based on the future time.

24. The system of claim 11, the memory further storing instructions to compare the estimated analyte level to a threshold value, wherein the alarm is output in response to the estimated analyte level satisfying the threshold value.

* * * * *